(12) United States Patent
Lewis et al.

(10) Patent No.: US 8,691,791 B2
(45) Date of Patent: Apr. 8, 2014

(54) MICROSPHERES FOR TREATMENT OF BRAIN TUMORS

(75) Inventors: Andrew Lennard Lewis, Surrey (GB); Yiqing Tang, Surrey (GB); Peter William Stratford, Surrey (GB)

(73) Assignee: Biocompatibles UK Limited, Surrey (GB)

( * ) Notice: Subject to any disclaimer, the term of this patent is extended or adjusted under 35 U.S.C. 154(b) by 200 days.

(21) Appl. No.: 12/089,797

(22) PCT Filed: Oct. 10, 2007

(86) PCT No.: PCT/EP2007/060793
§ 371 (c)(1),
(2), (4) Date: May 15, 2008

(87) PCT Pub. No.: WO2008/128580
PCT Pub. Date: Oct. 30, 2008

(65) Prior Publication Data
US 2010/0160246 A1    Jun. 24, 2010

(30) Foreign Application Priority Data

Apr. 24, 2007  (EP) .................................... 07106852

(51) Int. Cl.
*A61K 9/16* (2006.01)
*A61K 31/734* (2006.01)
*C08B 37/04* (2006.01)
*C08B 37/00* (2006.01)

(52) U.S. Cl.
CPC ................ *A61K 31/734* (2013.01); *A61K 9/16* (2013.01); *C08B 37/0006* (2013.01)
USPC ............................................... 514/54; 536/3

(58) Field of Classification Search
None
See application file for complete search history.

(56) References Cited

U.S. PATENT DOCUMENTS

| | | | | |
|---|---|---|---|---|
| 6,039,976 | A * | 3/2000 | Mehra et al. ................... | 424/480 |
| 7,041,241 | B2 * | 5/2006 | Faisant et al. ................... | 264/4.1 |
| 7,186,413 | B2 * | 3/2007 | Bouhadir et al. ............. | 424/400 |
| 7,442,385 | B2 * | 10/2008 | Lewis et al. ................... | 424/426 |
| 2002/0081339 | A1 * | 6/2002 | Menei et al. ................... | 424/649 |
| 2007/0275991 | A1 * | 11/2007 | Lewis et al. ................... | 514/283 |
| 2009/0022804 | A1 * | 1/2009 | Lewis et al. ................... | 424/486 |

FOREIGN PATENT DOCUMENTS

| | | | | |
|---|---|---|---|---|
| WO | 2004/071495 | A1 | 8/2004 | |
| WO | WO2004/071495 | * | 8/2004 | ............... A61K 9/16 |
| WO | 2006/027567 | A2 | 3/2006 | |
| WO | WO2006/027567 | * | 3/2006 | ............... A61K 9/16 |

OTHER PUBLICATIONS

U.S. Appl. No. 12/672,031, filed Mar. 2010, Lewis, Andrew Lennard.*
Lesniak et al., "Local Delivery of Doxorubicin for the Treatment of Malignant Brain Tumors in Rats" Anticancer Research (2005) vol. 25 No. 6B, pp. 3825-3831.*
Freund et al, Experimental investigation of doxorubicin and irinotecan loaded microspheres for intratumoral treatment of glioma, 58th Annual Meeting of the German Society of Neurosurgery (Apr. 26-29, 2007, Leipzig), 1-2, published on-line Nov. 4, 2007.
H.Brem, et al, Biodegradable polymer implants to treat brain tumors, Journal of Controlled Release, 2001, 63-67, vol. 74(1-3), Johns Hopkins University School of Medicine Department of Neurological Surgery, Baltimore, MD.
D.Emerich et al, Injection of Chemotherapeutic Microspheres and Glioma IV: Eradicating Tumors in Rats, Cell Transplantation, 2002, 47-54, vol. 11(1), Cognizant Communication Corporation.
P.Menei, et al, Implantable drug-releasing biodegradable microspheres for local treatment of brain glioma, Acta Neurochir 2003, 51-55, vol. 88, Springer-Verlag, Austria.
V.Roullin, et al, Influence of 5-Fluorouracil-Loaded Microsphere Formulation of Efficient Rat Glioma Radiosensitization, Pharmaceutical Research, Sep. 2004, 1558-1563, vol. 21(9), Springer Science-Business Media.
P.Menei, et al, Stereotaxic Implantation of 5-Fluorouracil-Releasing Microspheres in Malignant Glioma, American Cancer Society, Jan. 15, 2004, 405-410, vol. 100(2).
R.Cheung et al, A new approach to the in vivo and in vitro investigation of drug release from locoregionally delivered microspheres, Journal of Controlled Release, 2004, 122-133, vol. 100(1), Johns Hopkins University School of Medicine Department of Neurological Surgery, Baltimore, MD.
W.Hsu et al, Local delivery of interleukin-2 and adriamycin is synergistic in the treatment of experimental malignant glioma, Journal of Neuro-Oncoloy, 2005, 135-140, vol. 74(2), Springer Science Business Media.
D.Liu et al, Pharmacokinetics of doxorubicin alginate microspheres and evaluation of its hepatic arterial embolization in vivo, Aeta Pharmaceutica Sinica, 2006, 778-783, vol. 41(8).
K.Hong, et al, New Intra-arterial Drug Delivery System for the Treatment of Liver Cancer: Preclinical Assessment in a Rabbit Model of Liver Cancer, Clinical Cancer Res, Apr. 15, 2006, 2563-2567, vol. 12(8), www.aacrjournals.org.

* cited by examiner

*Primary Examiner* — Eric S Olson
(74) *Attorney, Agent, or Firm* — Sughrue Mion, PLLC

(57) ABSTRACT

There is provided a new use of microspheres comprising a water-insoluble, water-swellable polymer which is anionically charged at pH7, and electrostatically associated with the polymer, in releasable form, a cationically charged chemotherapeutic agent, in the manufacture of a composition for use in the treatment of a brain tumor, wherein in the treatment the composition is introduced into the brain and the chemotherapeutic agent is released from the microspheres, wherein the microspheres, when equilibrated in water at 37° C., comprise at least 40 wt % water based on weight of polymer plus water. Compositions comprising the microspheres and methods for the treatment of brain tumors are also provided.

25 Claims, 17 Drawing Sheets

MICROSPHERES FOR TREATMENT OF BRAIN TUMORS

The present invention relates to the use of microspheres for the treatment of a brain tumour, in which the microspheres comprise a water-insoluble polymer and a cationically charged chemotherapeutic agent. A composition comprising microspheres and a method of treatment of a brain tumour are also provided.

Glioblastoma multiforme (GBM), also known as grade 4 astrocytoma, is the most common and aggressive type of primary brain tumour, accounting for 52% of all primary brain tumour cases and 20% of all intracranial tumours. Treatment can involve chemotherapy, radiotherapy and surgery, which are known as palliative measures. The five year survival rate of the disease has remained unchanged over the past 30 years, and stands at less than 3%. Even with complete surgical resection of the tumour, combined with the best available treatment, the survival rate for GBM remains very low.

A typical treatment involves a resection with maximal tumour-free margins ("debulking") along with external beam radiation and chemotherapy. Total cranial irradiation (4500 cGy) with a boosted dose (1500 to 2000 cGy) at the site of the tumour, can increase survival by 5 months. The addition of the chemotherapeutic agent carmustine alone increases survival slightly. Most oncologists prefer a combination chemotherapy consisting of procarbazine, lomustine, and vincristine (PCV regimen). Another combination includes carboplatin and cisplatin. Their efficacy is limited, and toxicity, particularly with the PCV regimen, can be considerable. Brachytherapy (implantation of radioactive beads or needles) and high-dose focus radiotherapy (stereotactic radiosurgery) have not shown to increase survival times.

In a large phase III trial, implantation of BiCNU-impregnated wafers (trade name Glidel Wafers) at the time of primary resection, improved median survival to 13.9 months, compared with only 11.6 months for placebo wafers (P=0.03), in newly diagnosed patients with malignant glioma.

Tumour recurrence after surgery or radiation is almost inevitable, usually within 2 cm of the original site, and around 10% of patients may develop new lesions at distant sites. Re-operation or brachytherapy has been attempted, with uncertain results.

Typically, all untreated patients die within 3 months. Increasing age (>60 years of age) carries a worse prognostic risk. Death is usually due to cerebral edema or increased intracranial pressure.

With standard treatment (radiotherapy and temozolomide), the median survival is approximately 14 months (Stupp R. et al. "Radiotherapy plus concomitant and adjuvant temozolomide for glioblastoma", N Engl J Med 352 (10): 987-96). Less than 10% of these patients survive past 5 years. There is therefore a desire to provide more effective treatments for brain tumours.

There has been significant work reported on the development of drug delivery systems for the local delivery of therapeutics directly into tumour sites within the brain. The BCNU Gliadel wafer, as described above, is one of the few systems that has been commercialised. There have been many other systems described in the literature, and in particular, drug delivering microspheres have been a popular choice of design given that they can be injected relatively easily and designed to control the release of a wide range of therapeutic agents.

For instance, Brem et al describe the encapsulation of BCNU into biodegradable PLGA microspheres for use in treating glioma (J. Control Release 2001 Jul. 6; 74(1-3):63-7) and note the need to expand to other chemotherapeutics and combinations thereof to treat BCNU-resistant tumours. Emerich et al (Cell Transplant 2002; 11(1):47-54) describe polymer microspheres that could be easily injected into the brain to provide a local and sustained delivery of chemotherapeutics to a tumour or surrounding tissue subject to high rates of tumour recurrence following surgery.

There has been considerable interest in the delivery of 5-FU from microspheres for use in the treatment of glioma. The group of Philippe Menei in France has evaluated these systems in detail (Acta Neurochir Suppl. 2003; 88:51-5). The group found 5-FU controlled delivery was a promising strategy for radiosensitizing gliomas (Pharm Res. 2004 September; 21(9):1558-63) and that drug delivery system formulation was unambiguously implicated in both the response to treatment and the limitation of toxic side effects.

Furthermore, Menei et al have developed a new method of drug delivery into the brain using implantable, biodegradable microspheres (Cancer 2004 Jan. 15; 100(2):405-10). In this study, the microspheres were implanted by stereotaxy into deeply situated and inoperable brain tumours.

Cheung et al have described methods for evaluation of locoregional release of doxorubicin from microspheres (J. Control Release 2004 Nov. 5; 100(1):121-33). Brem et al have delivered doxorubicin from biodegradable microspheres and shown that both doxorubicin and IL-2, when delivered locally, are effective monotherapeutic agents against experimental intracranial gliosarcoma. The combination doxorubicin and IL-2 therapy was more effective than either agent alone (J. Neurooncol 2005 September; 74(2): 135-40).

Others have evaluated alginate microspheres loaded with doxorubicin (Yao Xue Xue Bao. 2006 August; 41(8):778-83), or PVA hydrogel beads modified with sulphonate groups loaded with doxorubicin (Clin Cancer Res. 2006 Apr. 15; 12(8):2563-7), for chemoembolization of the liver and demonstrated a sustained delivery in vivo. These systems use the ion-exchange properties of the polymer to sequester cationically charged drugs such as doxorubicin hydrochloride, and provide a method of controlled and sustained post intra-arterial delivery to a specific site within the body. We have also, in our previously published patent applications WO04/071495 and WO06/027567, described microspheres comprising water-insoluble polymer, having an overall anionic charge and electrostatically associated with the polymer an anthracycline or camptothecin compound. The microspheres may be used to embolise tumours, for instance a hepatocellular carcinoma.

There remains an unmet need to provide a drug delivery system for the treatment of brain tumours which is efficacious against even the most aggressive of tumours whilst avoiding the unwanted side effects associated with the prior art. The delivery system needs to be easily targeted to the brain tumour.

In accordance with this unmet need, we provide in this invention use of microspheres comprising a water-insoluble, water-swellable polymer which is anionically charged at pH7, and electrostatically associated with the polymer, in releasable form, a cationically charged chemotherapeutic agent, in the manufacture of a composition for use in the treatment of a brain tumour, wherein in the treatment the composition is introduced into the brain and the chemotherapeutic agent is released from the microspheres, wherein the microspheres, when equilibrated in water at 37° C. comprise at least 40 wt % water based on weight of polymer plus water.

Also provided by this invention is a composition comprising microspheres for use in the treatment of a brain tumour, wherein in the treatment the composition is introduced into the brain and the chemotherapeutic agent is released from the microspheres, wherein the microspheres, when equilibrated in water at 37° C., comprise at least 40 wt % water based on weight of polymer plus water, and comprise a water-insoluble, water-swellable polymer which is anionically charged at pH7, and electrostatically associated with the polymer, in releasable form, a cationically charged chemotherapeutic agent.

The invention is also directed to a method of treatment of a brain tumour comprising introducing into the brain a composition comprising microspheres, wherein the microspheres comprise a water-insoluble, water-swellable polymer which is anionically charged at pH7, and electrostatically associated with the polymer, in releasable form, a cationically charged chemotherapeutic agent, wherein in the treatment the chemotherapeutic agent is released from the microspheres; and wherein when equilibrated in water at 37° C., the microspheres comprise at least 40 wt % water based on weight of polymer plus water.

The microspheres, as defined above, release the cationically charged chemotherapeutic agent via an ion-exchange mechanism, and thereby act as a depot for the controlled delivery of the cationically charged chemotherapeutic agent to a brain tumour. The agent may be delivered to the resection margin of a debulked brain tumour, or intra-tumourally for unresectable tumours by stereotaxy. The deformable nature of the polymer which comprises the microspheres enables the microspheres to be deliverable by needles for direct injection into the desired site. The microspheres may be degradable, non-degradable, or even combined with a radiosensitizing agent to enable the microsphere treatment to be combined with radiotherapy.

The polymer is a water-insoluble material. Although it may be biodegradable, so that drug may be released substantially by erosion from the surface of the polymer matrix, preferably the polymer is substantially biostable (i.e. non-biodegradable).

The polymer is water-swellable. Water-swellable polymer in the present invention has a equilibrium water content, when swollen in water at 37° C., measured by gravimetric analysis of at least 40 wt %, preferably in the range of 40 to 99 wt %, most preferably 75 to 95%.

In a preferred embodiment of the invention, the composition which is introduced into the brain, is in the form of a suspension of microspheres of water-swollen water-insoluble polymer in a liquid carrier. Typically, the microspheres have sizes when equilibrated in water at 37° C., in the range 1-1000 μm, more preferably in the range 50 to 500 μm, most preferably in the range 100-300 μm. Preferably the microspheres are substantially spherical in shape. The diameter is preferably determined by measurement of the microsphere size prior to loading with the cationically charged chemotherapeutic agent. Although the microspheres are preferably substantially spherical, they may be spheroidal or even less regular in shape. The diameter of a non-spherical microsphere is its largest diameter.

Generally the polymer is covalently crosslinked, although it may be appropriate for the polymer to be ionically crosslinked, at least in part.

Polymers which are derived from natural sources, such as albumin, alginate, gelatin, starch, chitosan or collagen may be used in one embodiment of the invention. Alginate is particularly preferred. Alginate microspheres are typically prepared from super-pure alginate with either High G or High M content by extrusion of an alginate solution of specific concentration into a gelling bath of metal (e.g. calcium or barium) ions, as further described in Example 8.

In another embodiment the polymer is formed by polymerising ethylenically unsaturated monomers in the presence of di- or higher-functional crosslinking monomers. The ethylenically unsaturated monomers may include an ionic (including zwitterionic) monomer.

Copolymers of hydroxyethyl methacrylate, acrylic acid and cross-linking monomer, such as ethylene glycol dimethacrylate or methylene bisacrylamide, as used for etafilcon A based contact lenses may be used. Copolymers of N-acryloyl-2-amino-2-hydroxymethyl-propane-1,3-diol and N,N-bisacrylamide may also be used.

Other polymers are cross-linked styrenic polymers e.g. with ionic substituents, of the type used as separation media or as ion exchange media.

Another type of polymer which may be used to form the water-swellable water-insoluble matrix is cross-linked polyvinyl alcohol. The polymer may, for instance, be crosslinked using aldehyde-type crosslinking agents such as glutaraldehyde. For such products, the polyvinyl alcohol (PVA) may be rendered ionic by providing pendant ionic groups by reacting a functional ionic group containing compound with the hydroxyl groups. Examples of suitable functional groups for reaction with the hydroxyl groups are acylating agents, such as carboxylic acids or derivatives thereof, or other acidic groups which may form esters.

The polyvinyl alcohol may alternatively be a copolymer of vinyl alcohol and an anionic acrylic monomer such as an acrylic acid, of the type used as super-absorbent polymers.

The invention is of particular value where the polymer matrix is formed from a polyvinyl alcohol macromer, having more than one ethylenically unsaturated pendant group per molecule, by radical polymerisation of the ethylenic groups. Preferably the PVA macromer is copolymerised with ethylenically unsaturated monomers for instance including a non-ionic and/or ionic monomer including anionic monomer.

The PVA macromer may be formed, for instance, by providing PVA polymer, of a suitable molecular weight such as in the range 1000 to 500,000 D, preferably 10,000 to 100,000 D, with pendant vinylic or acrylic groups. Pendant acrylic groups may be provided, for instance, by reacting acrylic or methacrylic acid with PVA to form ester linkages through some of the hydroxyl groups. Other methods for attaching vinylic groups capable of polymerisation onto polyvinyl alcohol are described in, for instance, U.S. Pat. No. 4,978,713 and, preferably, U.S. Pat. Nos. 5,508,317 and 5,583,163. Thus the preferred macromer comprises a backbone of polyvinyl alcohol to which is linked, via a cyclic acetal linkage, an (alk)acrylaminoalkyl moiety. Example 1 describes the synthesis of an example of such a macromer known by the approved named nelfilcon B. Preferably the PVA macromers have about 2 to 20 pendant ethylenic groups per molecule, for instance 5 to 10.

Where PVA macromers are copolymerised with ethylenically unsaturated monomers including an ionic monomer, the ionic monomer preferably has the general formula I $$Y^1BQ^1 \qquad\qquad I$$

in which $Y^1$ is selected from

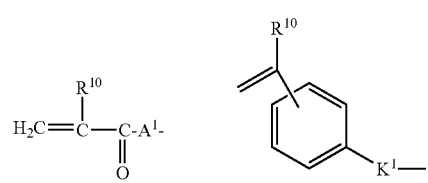

$CH_2=C(R^{10})-CH_2-O-$, $CH_2=C(R^{10})-CH_2OC(O)-$, $CH_2=C(R^{10})OC(O)-$, $CH_2=C(R^{10})-O-$, $CH_2=C(R^{10})CH_2OC(O)N(R^{11})-$, $R^{12}OOCCR^{10}=CR^{10}C(O)-O-$, $R^{10}CH=CHC(O)O-$, $R^{10}CH=C(COOR^{12})CH_2-C(O)-O-$,

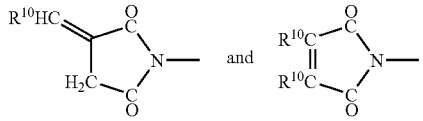

wherein:

$R^{10}$ is hydrogen or a $C_1$-$C_4$ alkyl group;

$R^{11}$ is hydrogen or a $C_1$-$C_4$ alkyl group;

$R^{12}$ is hydrogen or a $C_{1-4}$ alkyl group or $BQ^1$ where B and $Q^1$ are as defined below;

$A^1$ is $-O-$ or $-NR^{11}-$;

$K^1$ is a group $-(CH_2)_rOC(O)-$, $-(CH_2)_rC(O)O-$, $-(CH_2)_rOC(O)O-$, $-(CH_2)_rNR^{13}-$, $-(CH_2)_rNR^{13}C(O)-$, $-(CH_2)_rC(O)NR^{13}-$, $-(CH_2)_rNR^{13}C(O)O-$, $-(CH_2)_rOC(O)NR^{13}-$, $-(CH_2)_rNR^{13}C(O)NR^{13}-$ (in which the groups $R^{13}$ are the same or different), $-(CH_2)_{10}-$, $-(CH_2)_rSO_3-$, or, optionally in combination with B, a valence bond and r is from 1 to 12 and $R^{13}$ is hydrogen or a $C_1$-$C_4$ alkyl group;

B is a straight or branched alkanediyl, oxaalkylene, alkanediyloxaalkanediyl, or alkanediyloligo(oxaalkanediyl) chain optionally containing one or more fluorine atoms up to and including perfluorinated chains or, if $Q^1$ or $Y^1$ contains a terminal carbon atom bonded to B a valence bond; and $Q^1$ is an ionic group.

Such a compound including an anionic group $Q^1$ is preferably included.

An anionic group $Q^1$ may be, for instance, a carboxylate, carbonate, sulphonate, sulphate, nitrate, phosphonate or phosphate group. The monomer may be polymerised as the free acid or in salt form. Preferably the $pK_a$ of the conjugate acid is less than 5.

A suitable cationic group $Q^1$ is preferably a group $N^+R^{14}_3$, $P^+R^{15}_3$ or $S^+R^{15}_2$ in which the groups $R^{14}$ are the same or different and are each hydrogen, $C_{1-4}$-alkyl or aryl (preferably phenyl) or two of the groups $R^{14}$ together with the heteroatom to which they are attached form a saturated or unsaturated heterocyclic ring containing from 5 to 7 atoms. The groups $R^{15}$ are each $OR^{14}$ or $R^{14}$. Preferably the cationic group is permanently cationic, that is each $R^{14}$ is other than hydrogen. Preferably a cationic group Q is $N^+R^{14}_3$ in which each $R^{14}$ is $C_{1-4}$-alkyl, preferably methyl.

A zwitterionic group $Q^1$ may have an overall charge, for instance by having a divalent centre of anionic charge and monovalent centre of cationic charge or vice-versa or by having two centres of cationic charge and one centre of anionic charge or vice-versa. Preferably, however, the zwitterion has no overall charge and most preferably has a centre of monovalent cationic charge and a centre of monovalent anionic charge.

Examples of zwitterionic groups which may be used as Q in the present invention are disclosed in WO-A-0029481.

Where the ethylenically unsaturated monomer includes zwitterionic monomer, for instance, this may increase the hydrophilicity, lubricity, biocompatibility and/or haemocompatibility of the particles. Suitable zwitterionic monomers are described in our earlier publications WO-A-9207885, WO-A-9416748, WO-A-9416749 and WO-A-9520407. Preferably a zwitterionic monomer is 2-methacryloyloxyethyl phosphorylcholine (MPC).

In the monomer of general formula I preferably $Y^1$ is a group $CH_2=CR^{10}COA^1$- in which $R^{10}$ is H or methyl, preferably methyl, and in which $A^1$ is preferably NH. B is preferably an alkanediyl group of 1 to 12, preferably 2 to 6 carbon atoms. Such monomers are acrylic monomers.

There may be included in the ethylenically unsaturated monomer diluent monomer, for instance non-ionic monomer. Such a monomer may be useful to control the $pK_a$ of the acid groups, to control the hydrophilicity or hydrophobicity of the product, to provide hydrophobic regions in the polymer, or merely to act as inert diluent. Examples of non-ionic diluent monomer are, for instance, alkyl (alk) acrylates and (alk) acrylamides, especially such compounds having alkyl groups with 1 to 12 carbon atoms, hydroxy, and di-hydroxy-substituted alkyl(alk) acrylates and -(alk) acrylamides, vinyl lactams, styrene and other aromatic monomers.

In the polymer matrix, the level of anion is preferably in the range 0.1 to 10 meq $g^{-1}$, preferably at least 1.0 meq $g^{-1}$. Preferred anions are derived from strong acids, such as sulphates, sulphonates, phosphates and phosphonates.

Where PVA macromer is copolymerised with other ethylenically unsaturated monomers, the weight ratio of PVA macromer to other monomer is preferably in the range of 50:1 to 1:5, more preferably in the range 20:1 to 1:2.

In the ethylenically unsaturated monomer the anionic monomer is preferably present in an amount in the range 10 to 100 mole %, preferably at least 25 mole %.

The crosslinked polymer may be formed as such in particulate form, for instance by polymerising droplets of ethylenically unsaturated monomer in a dispersed phase in a continuous immiscible carrier. This is especially suitable for the polyvinyl alcohol macromer-based polymerisation. Examples of suitable water-in-oil polymerisations to produce microspheres having the desired size, when swollen, are known. For instance U.S. Pat. No. 4,224,427 describes processes for forming uniform spherical beads (microspheres) of up to 5 mm in diameter, by dispersing water-soluble monomers into a continuous solvent phase, in a presence of suspending agents. Cross-linking a preformed polymerising droplets of a dispersion can also be used. Cross-linking a preformed polymer in droplets of a dispersion can also be used. Stabilisers and surfactants may be present to provide control over the size of the dispersed phase particles. After polymerisation, and/or cross-linking, the crosslinked microspheres are recovered by known means, and are washed and optionally sterilised. Preferably the microspheres are swollen in an aqueous liquid, and classified according to their size.

The cationically charged chemotherapeutic agent (hereinafter also referred to as "active" or "drug") is associated with the polymer preferably so as to allow controlled release of the active over a period. This period may be from several minutes to weeks, preferably at least up to a few days, preferably up to 72 hours. The active is electrostatically bonded to the polymer. The presence of anionic groups in the polymer allows control of release of cationically charged active.

In the invention it is important that the drug is not covalently attached to the polymer matrix.

The active may be incorporated into the polymer matrix by a variety of techniques. In one method, the active may be mixed with a precursor of the polymer, for instance a monomer or macromer mixture or a cross-linkable polymer and cross-linker mixture, prior to polymerising or crosslinking. Alternatively, the active may be loaded into the polymer after it has been crosslinked. For instance, particulate dried polymer may be swollen in a solution of active, preferably in water or in an alcohol such as ethanol, optionally with subsequent removal of non-absorbed agent and/or evaporation of solvent. A solution of the active, in an organic solvent such as an alcohol, or, more preferably, in water, may be sprayed onto a moving bed of microspheres, whereby drug is absorbed into the body of the microspheres with simultaneous solvent removal. Most conveniently, we have found that it is possible merely to contact swollen microspheres suspended in a continuous liquid vehicle, such as water, with an aqueous alcoholic solution of drug, over a period, whereby drug becomes absorbed into the body of the microspheres. Techniques to fix the drug in the microspheres may increase loading levels, for instance, precipitation by shifting the pH of the loading suspension to a value at which the active is in a relatively insoluble form. The swelling vehicle may subsequently be removed or, conveniently, may be retained with the microspheres as part of the product. The swollen microspheres may be used in swollen form in the form of a slurry, i.e. without any or much liquid outside the swollen microspheres. Alternatively, the suspension of microspheres can be removed from any remaining drug loading solution and the microspheres dried by any of the classical techniques employed to dry pharmaceutical-based products. This could include, but is not limited to, air drying at room or elevated temperatures or under reduced pressure or vacuum; classical freeze-drying; atmospheric pressure-freeze drying; solution enhanced dispersion of supercritical fluids (SEDS). Alternatively the drug-loaded microspheres may be dehydrated using an organic solvent to replace water in a series of steps, followed by evaporation of the more volatile organic solvent. A solvent should be selected which is a non-solvent for the drug.

In brief, a typical classical freeze-drying process might proceed as follows: the sample is aliquoted into partially stoppered glass vials, which are placed on a cooled, temperature controlled shelf within the freeze dryer. The shelf temperature is reduced and the sample is frozen to a uniform, defined temperature. After complete freezing, the pressure in the dryer is lowered to a defined pressure to initiate primary drying. During the primary drying, water vapour is progressively removed from the frozen mass by sublimation whilst the shelf temperature is controlled at a constant, low temperature. Secondary drying is initiated by increasing the shelf temperature and reducing the chamber pressure further so that water absorbed to the semi-dried mass can be removed until the residual water content decreases to the desired level. The vials can be sealed, in situ, under a protective atmosphere if required.

Atmospheric pressure freeze-drying is accomplished by rapidly circulating very dry air over a frozen product. In comparison with the classical freeze-drying process, freeze-drying without a vacuum has a number of advantages. The circulating dry gas provides improved heat and mass transfer from the frozen sample, in the same way as washing dries quicker on a windy day. Most work in this area is concerned with food production, and it has been observed that there is an increased retention of volatile aromatic compounds, the potential benefits of this to the drying of biologicals is yet to be determined. Of particular interest is the fact that by using atmospheric spray-drying processes, instead of a cake, a fine, free-flowing powder is obtained. Particles can be obtained which have submicron diameters, this is ten-fold smaller than can be generally obtained by milling. The particulate nature, with its high surface area results in an easily rehydratable product, currently the fine control over microsphere size required for inhalable and transdermal applications is not possible, however there is potential in this area.

Although the composition may be made up from polymer and cationically charged chemotherapeutic agent (active) immediately before administration, it is preferred that the composition is preformed. Dried polymer-active microspheres may be hydrated immediately before use. Alternatively the composition which is supplied may be fully compounded and preferably comprises polymer microspheres with absorbed or adsorbed active compound and imbibed water e.g. physiological saline and extra-particulate liquid, for instance saline.

The level of active in the composition which is administered is preferably in the range 0.1 to 500 mg per ml composition, preferably 10 to 100 mg per ml. Preferably the treatment is repeated one to five times and for each dose the amount of active administered is in the range 0.1 to 100 mg per ml, preferably 10 to 100 mg per ml. The amount of composition administered in a normal treatment is in the range 1 to 6 ml. The total amount of active administered per dose is preferably in the range 10 to 1000 mg, more preferably 50 to 250 mg. Based on the release data as shown in the Examples below, the inventors believe this will give therapeutically effective concentrations in the tumour and that significant levels of intracellular delivery should take place whereby a therapeutic effect will be achieved. The adverse side effects of active administration should be avoided.

The chemotherapeutic agent (active) used in this invention may be any compound which is cationically charged and therapeutically active against brain tumours. The chemotherapeutic agent may be a prodrug, that is, a compound which is activated in vivo to form the active. The chemotherapeutic agent may alternatively be a radiosensitiser. For instance, Doxorubicin and 5-FU are both radiosensitising agents. A radiosensitiser is a compound which is activated by application of radiotherapy to the compound.

The active may be an anthracycline compound or an analogue thereof, which may comprise an anthraquinone group to which is attached an amine sugar. The amino group on the sugar is believed to associate with the anionic groups in the polymer matrix, to allow high levels of loading and controlled delivery after administration.

Examples of suitable anthracyclines have the general formula II

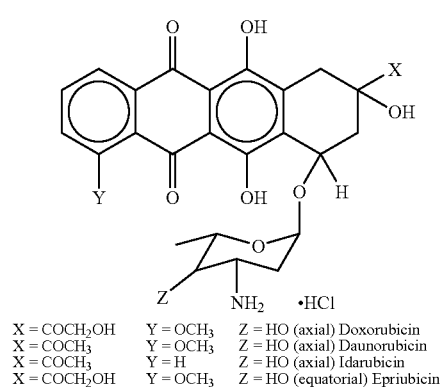

X = COCH$_2$OH  Y = OCH$_3$  Z = HO (axial) Doxorubicin
X = COCH$_3$     Y = OCH$_3$  Z = HO (axial) Daunorubicin
X = COCH$_3$     Y = H        Z = HO (axial) Idarubicin
X = COCH$_2$OH  Y = OCH$_3$  Z = HO (equatorial) Epriubicin We have found that doxorubicin, which has been thoroughly tested for efficacy on various tumours, has particularly interesting loading and release characteristics. The drug appears to have a particular affinity for poly(vinyl alcohol-graft-acrylamido propane sulphonic acid), so that high levels of doxorubicin are capable of incorporation into the polymer, and release over many days.

Anthracycline analogues that could be useful in the present invention include the anthacenedione family such as Mitoxantrone:

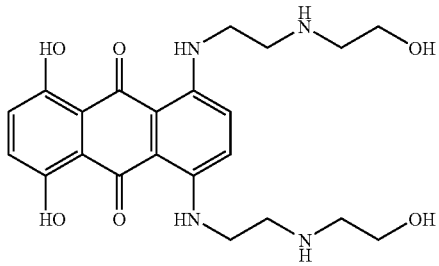 [SMILES: O=C1c2c(O)ccc(O)c2C(=O)c2c(NCCNCCO)ccc(NCCNCCO)c21]

Pixantrone (BBR 2887) is another aza-anthracenedione DNA intercalator. By inserting into replicating DNA these compounds stimulate topoisomerase II-mediated DNA cleavage. Unlike mitoxantrone, pixantrone is devoid of the 5,8-dihydroxy substitution groups thought to be responsible for the cardiac toxicity associated with these drugs.

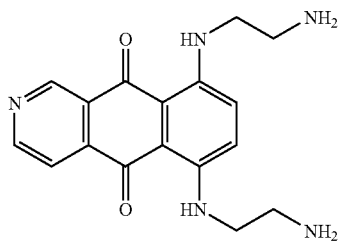

Structure of Pixantrone

AQ4N (Banoxantrone) is a novel agent with broad potential in treating a variety of cancers. AQ4N is a prodrug of AQ4 which targets hypoxic regions of tumours. In its prodrug form, AQ4 is far less toxic and able to penetrate the blood brain barrier. When present within the hypoxic areas that exist in many tumours, the AQ4 is converted to the highly potent AQ4N. The structure of AQ4 and AQ4N are shown below.

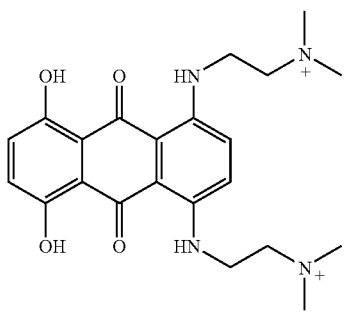

Structure of AQ4

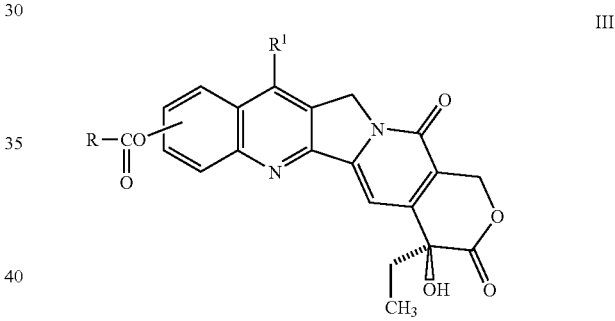

Structure of AQ4N

The active may be a camptothecin compound or analogue thereof.

The camptothecin compound is preferably at least sparingly water-soluble, for instance soluble to a concentration of at least 0.001 g/l in water at room temperature, preferably more than 0.002 g/l, more preferably more than 0.01 g/l. It is preferred that the camptothecin compound is cationically charged at pH7. The cationic group may be a primary amine group, but is preferably a secondary, tertiary or quaternary amine group.

One family of suitable compounds has the general formula III

III

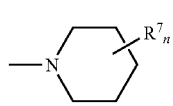

in which $R^1$ is H, lower ($C_{1-6}$) alkyl, optionally substituted by a hydroxyl, amine, alkoxy, halogen, acyl or acyloxy group or halogen; and R is chlorine or $NR^2R^3$ where $R^2$ and $R^3$ are the same or different and each represents a hydrogen atom, a substituted or unsubstituted $C_{1-4}$ alkyl group or a substituted or unsubstituted carbocyclic or heterocyclic group, or $R^2$ and $R^3$ together with the nitrogen atom to which they are attached form an optionally substituted heterocyclic ring which may be interrupted by —O—, —S— or —$NR^4$— in which $R^4$ is a hydrogen atom, a substituted or unsubstituted $C_{1-4}$ alkyl group or a substituted or unsubstituted phenyl group;

and wherein the group —O—CO—R is bonded to a carbon atom located in any of the 9, 10 or 11 positions in the A ring of the camptothecin compound, including salts thereof.

It is preferred for the group —O—CO—R to be joined at the 10 position.

$R^1$ is preferably $C_{1-4}$ alkyl, most preferably ethyl, and m is preferably 1.

A halogen atom R is, for instance, F, Cl, Br or I, preferably F or Cl. $R^1$ to $R^4$ may be methyl, ethyl, propyl, isopropyl, n-butyl, isobutyl and t-butyl, preferably methyl.

Substituents in R and $R^1$ are preferably selected from halogen atoms, hydroxy, $C_{1-4}$ alkoxy, phenoxy, $COOR^6$, $SO_3R^6$ and $PO_3(R^6)_2$, aryl, $NR^8R^9$ and $CONR^8R^9$, $QAOR^5$, $QANR^8R^9$ and $QAQR^5$ in which $R^5$ is $C_{1-4}$ alkyl or aryl; $R^6$ is hydrogen, halogen $C_{1-4}$ alkyl or $C_{1-4}$ alkoxy; $R^7$ is hydrogen, halogen or $C_{1-4}$ alkyl; $R^8$ and $R^9$ are the same or different and each is H, or $C_{1-4}$ alkyl or $R^8$ and $R^9$ together represent $C_{3-6}$ alkanediyl;

Q is OCO, or —COO— and A is $C_{2-4}$ alkanediyl.

Preferably R is $NR^2R^3$ where $R^2$ and $R^3$ together with the nitrogen atom form a 5 or 6 membered ring, preferably a saturated ring, with optional substituents. A substituent is preferably —$NR^8R^9$. In such a substituent $R^8$ and $R^9$ preferably together are $C_{4-6}$ alkanediyl. Such groups are basic and tend to be cationically charged at pH7. Most preferably R is

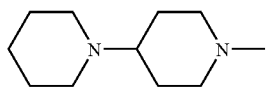

Another family of suitable compounds has the general formula IV

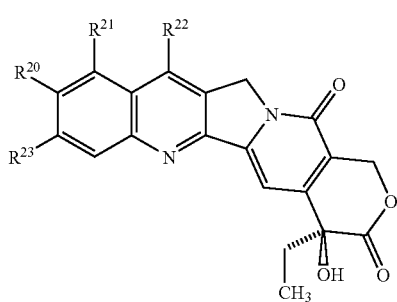

in which $R^{20}$ and $R^{23}$ are each hydroxy or hydrogen or together are $CH_2OCH_2$;

one of $R^{21}$ and $R^{22}$ is H and the other is $CH_2NR^{24}R^{25}$ where $R^{23}$ and $R^{24}$ are the same or different and each represents a hydrogen atom, a substituted or unsubstituted $C_{1-4}$ alkyl group or a substituted or unsubstituted carbocyclic or heterocyclic group, or $R^{23}$ and $R^{24}$ together with the nitrogen atom to which they are attached form a optionally substituted heterocyclic ring which may be interrupted by —O—, —S— or —$NR^4$— in which $R^4$ is a hydrogen atom, a substituted or unsubstituted $C_{1-4}$ alkyl group or a substituted or unsubstituted phenyl group; including salts and quaternary derivatives thereof. One example of a suitable compound of this formula is topotecan, in which $R^{20}$ is hydroxyl, $R^{22}$ and $R^{23}$ are hydrogen, $R^{21}$ is $CH_2NR^{24}R^{25}$ and $R^{24}$ and $R^{25}$ are both methyl.

Preferably, in the treatment as defined in this invention, the composition is injected into the brain, typically using a needle. Alternatively, a needleless injection system, as described in WO94/24263 may be used. US2007/0026081 describes how microspheres can be used for needleless injection.

The composition which is introduced into the brain may further comprise a radiosensitizing agent, such as Doxorubicin. This advantageously allows the treatment to be combined with radiotherapy. Alternatively, or as well as, the composition may comprise an imaging agent such as a conventional radiopaque agent, or a dye. The composition which is introduced may also be admixed with other therapeutic actives, or may be introduced separately but in combination with other actives.

The composition which is introduced into the brain is an aqueous suspension of swollen microspheres containing absorbed active. It is desirable to mix the suspension prior to delivery with any of the additional agents discussed above. Alternatively or additionally the microspheres may be preloaded with any of these additional agents.

It has been found that when injected into the brain, the microspheres have a tendency to be pushed out by the intratissular pressure. To overcome this problem, the composition which is introduced into the brain may additionally comprise a viscosity modifier. The viscosity modifier should increase the viscosity of the composition. The viscosity modifier may be, for instance, alginate, a carboxycellulosic or a biocompatible polymer such as PVP. When alginate is used as the viscosity modifier, the alginate advantageously forms a gel once injected by cross-linking with calcium ions which have diffused from surrounding tissue.

Alternatively, the composition may be injected into the brain using a rapid, high pressure system wherein the entire composition is injected using a syringe.

In one embodiment of this invention, the composition is injected into the resection margin of a debulked brain tumour. The resection margin comprises largely healthy tissue with some diffuse tumour. In this embodiment, preferably a less toxic active, such as irinotecan, is associated with the polymeric microspheres. A less toxic active is likely to be more selective for the diffuse tumour tissue and will thereby help to preserve vital brain tissue.

In a different embodiment of the invention, the composition is used to treat an unresectable brain tumour (i.e. a deep brain tumour which cannot be physically removed). In this embodiment, the composition is implanted into the tumour using a long needle, which is inserted directly into the centre of the tumour mass. Preferably, a more aggressive active is used to destroy the tumour mass. Doxorubicin, or one of its analogues is a suitable active in this embodiment of the invention.

Subjects treated in this invention are generally mammalian, and are preferably humans.

The invention is further illustrated in the following Examples. Some of the results are shown in the accompanying Figures, described in more detail in the Examples, but briefly described as follows FIG. 1 shows the loading of low and high AMPS Formulations of Bead Block with Doxorubicin;

Figure 14:
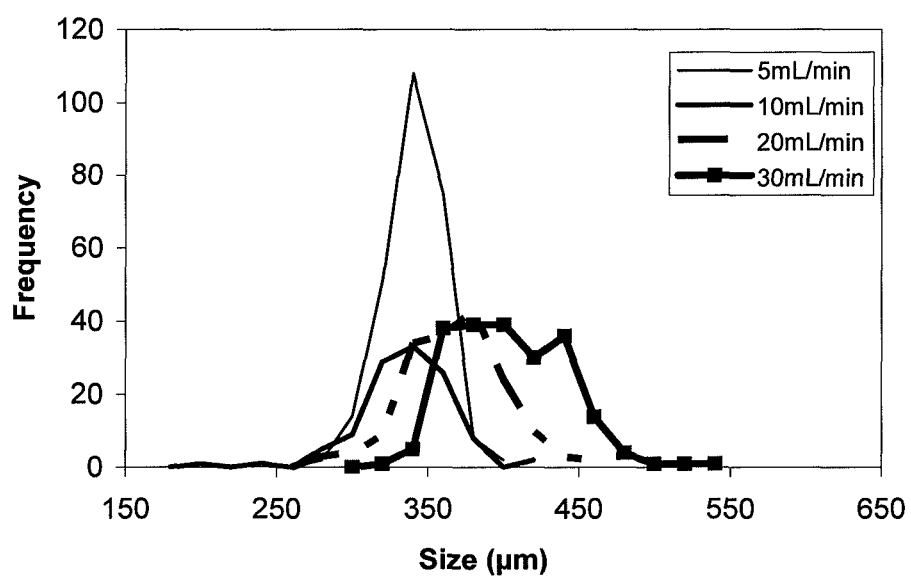
Figure 15:
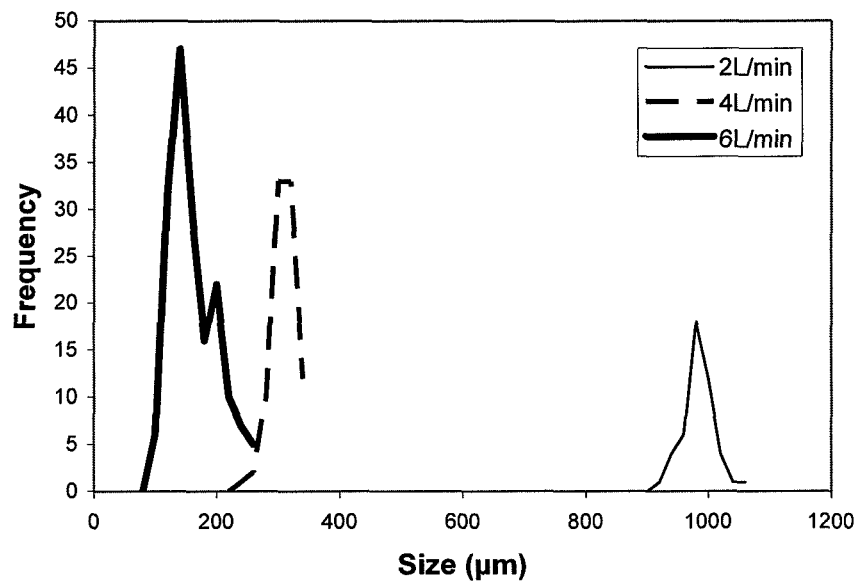
Figure 16:
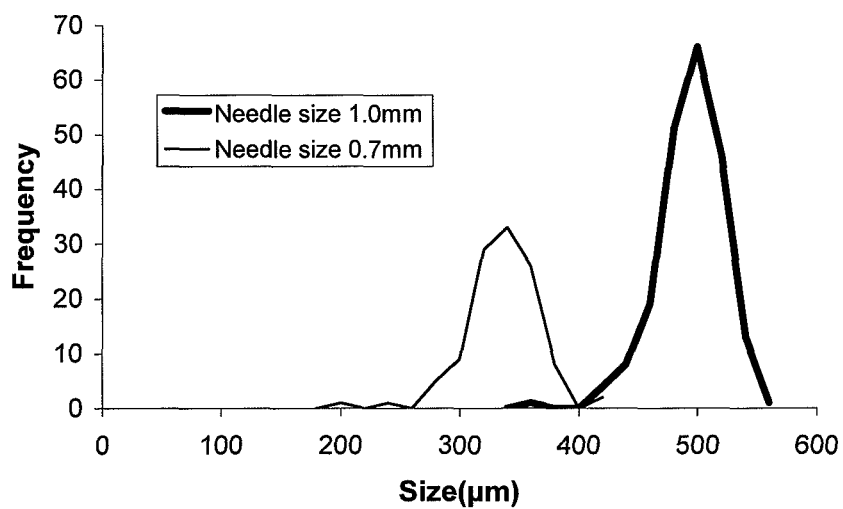
Figure 17:
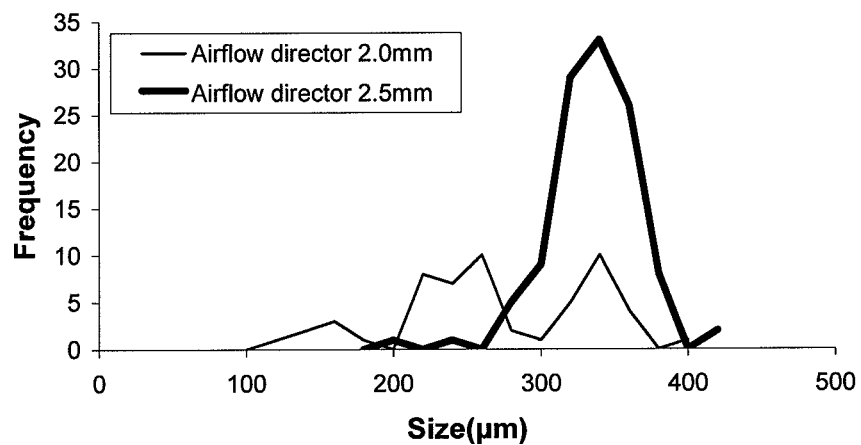
Figure 18:
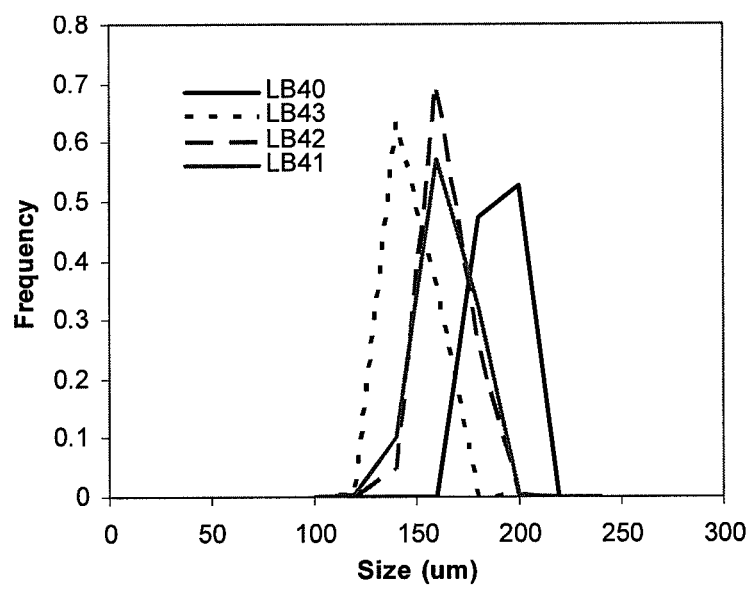
Figure 19:
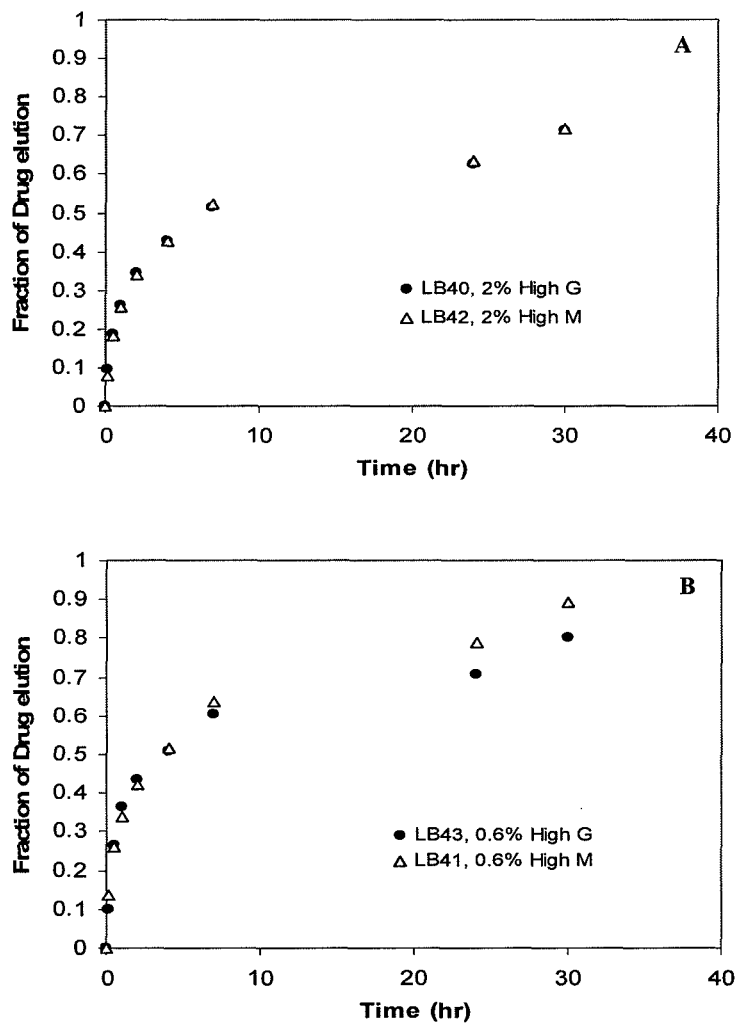
Figure 21:
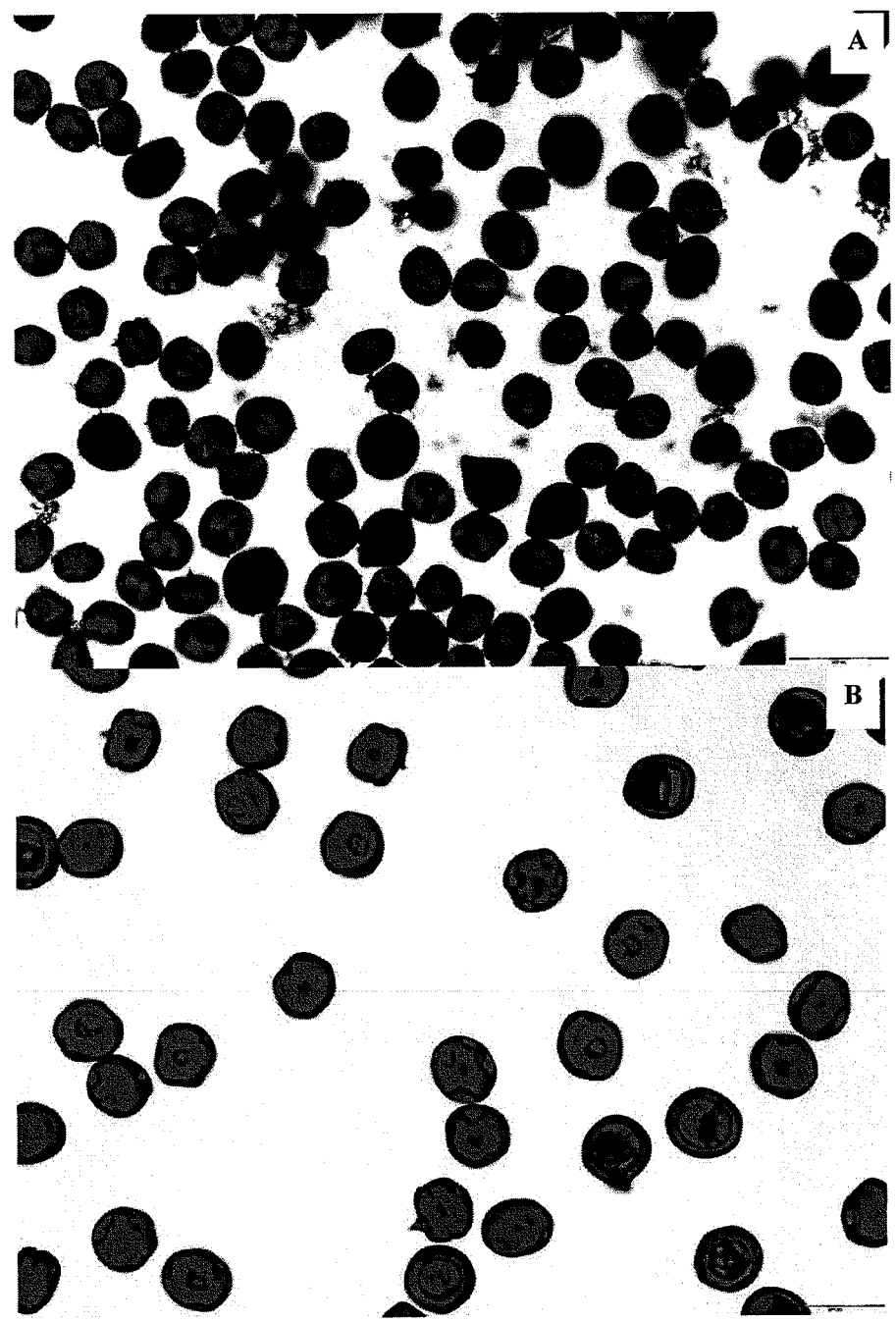
Figure 22:
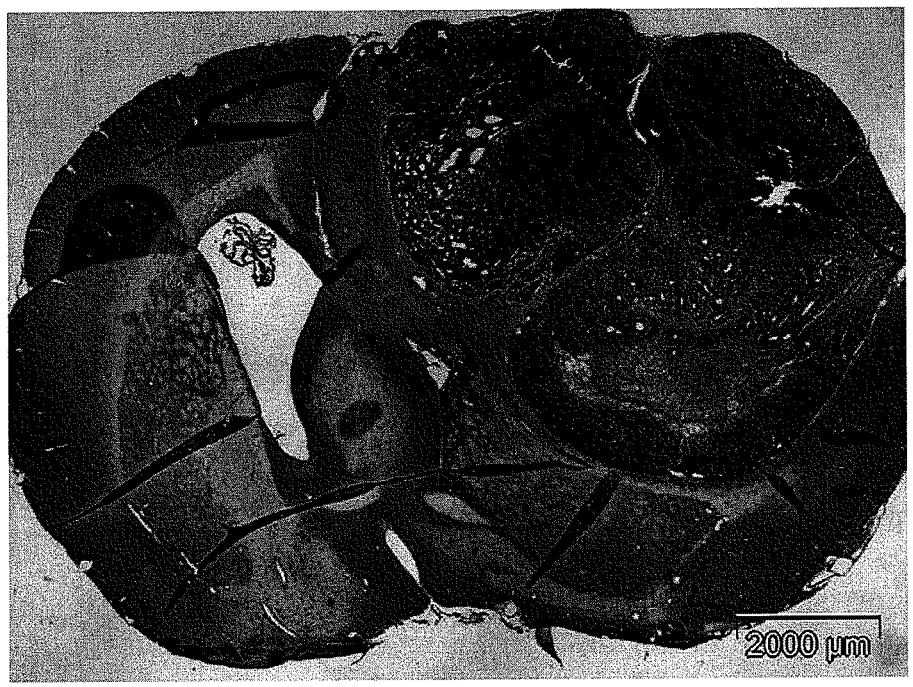
Figure 23:
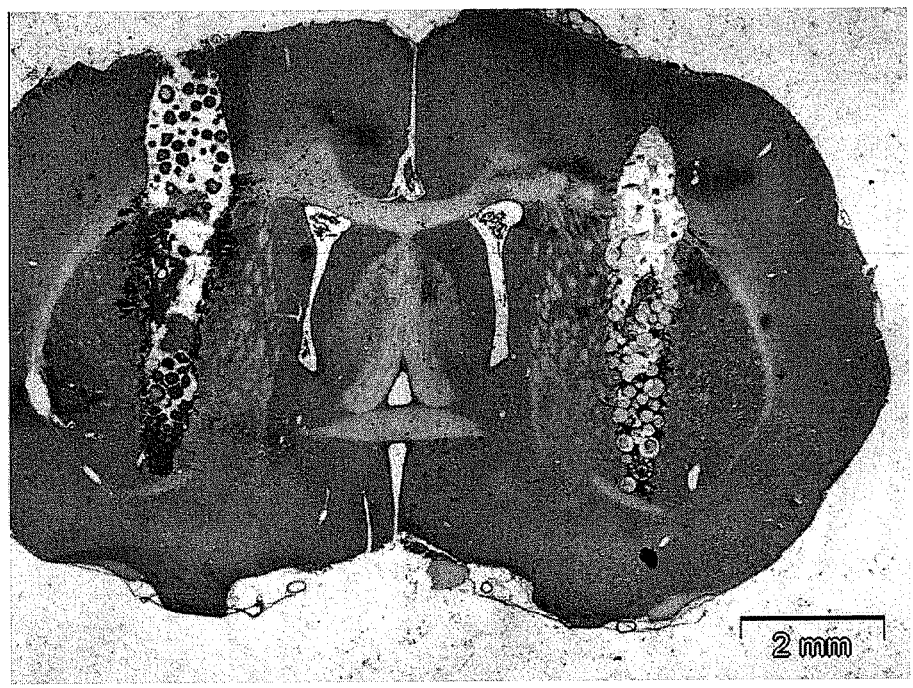
Figure 24:
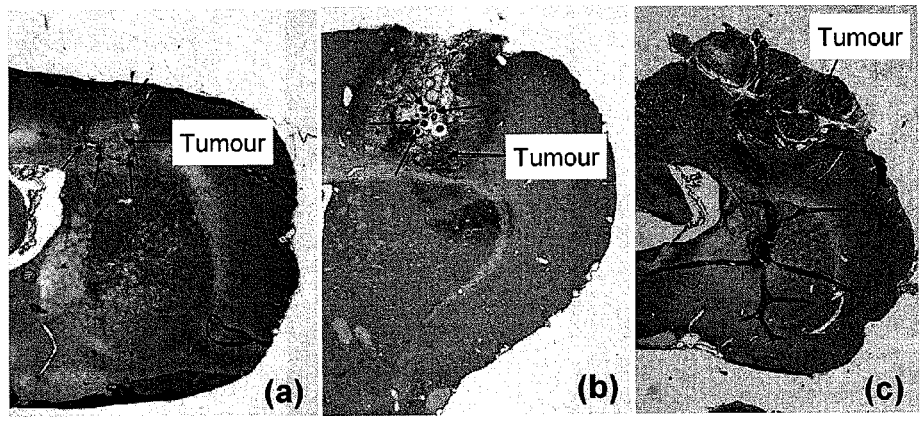
Figure 25:
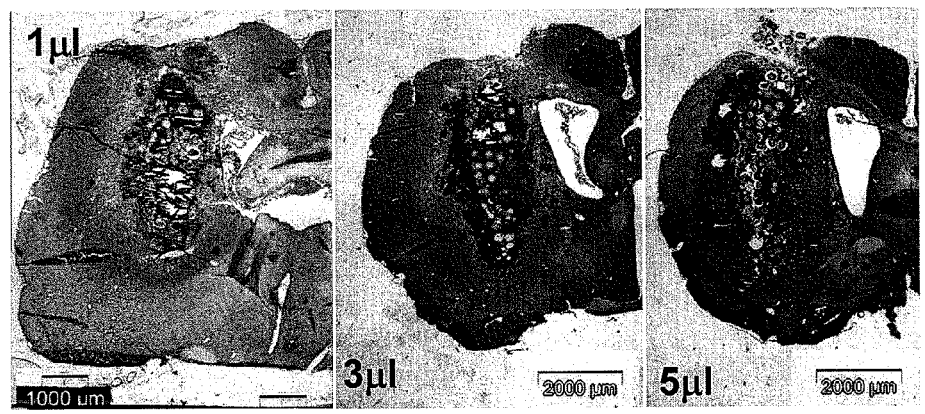
Figure 26:
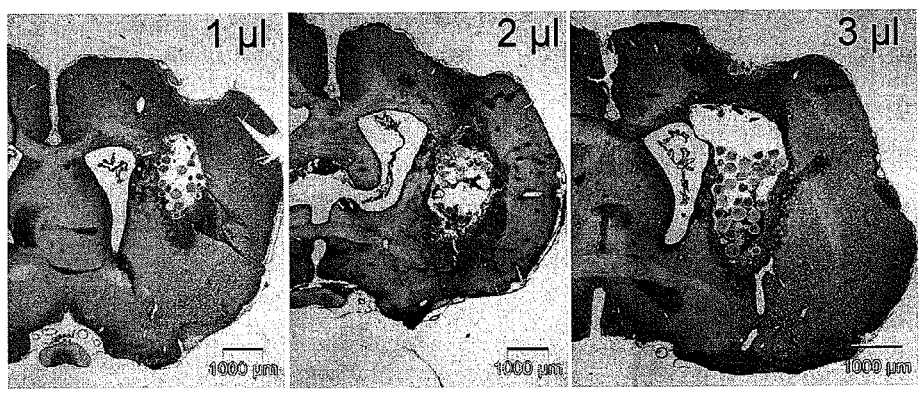
Figure 27:
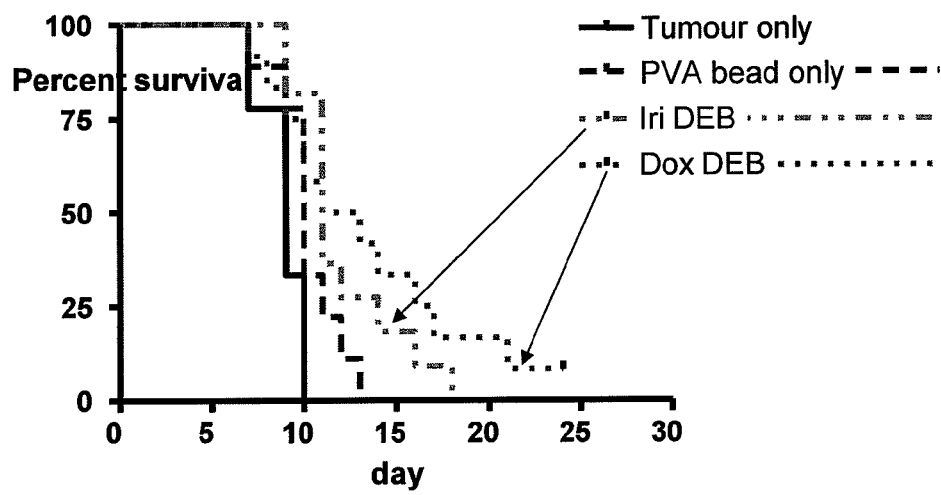
Figure 28:
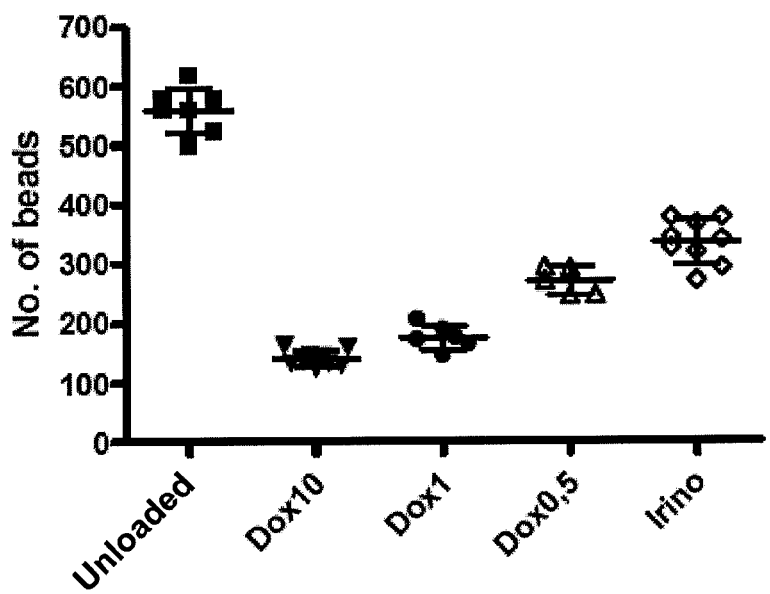
Figure 29:
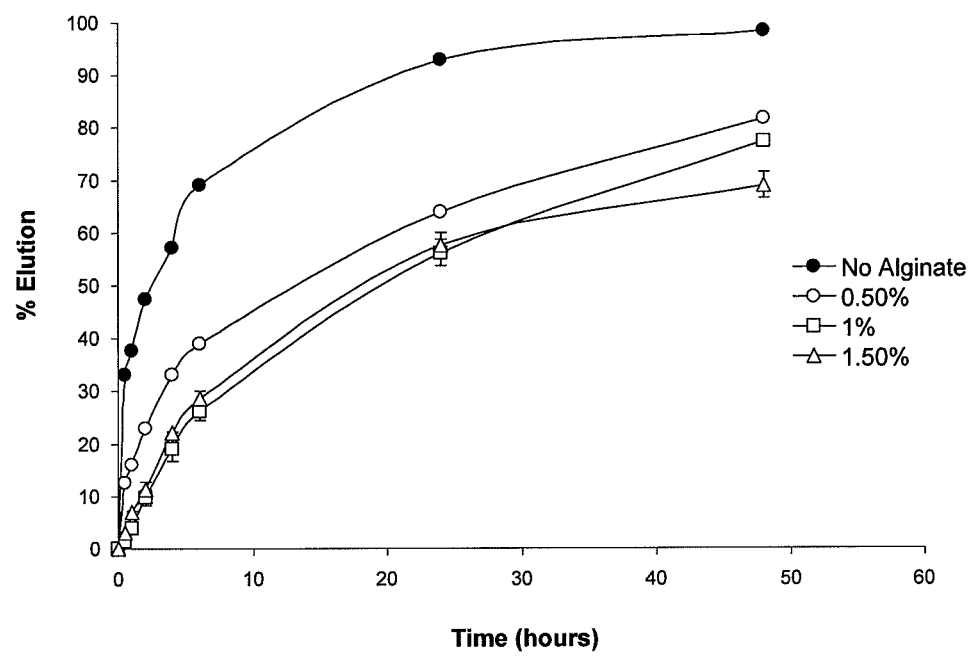

FIG. 14 compares the size of the alginate beads produced with different injection rates;

FIG. 15 compares the sizes of alginate beads produced with different airflow rates;

FIG. 16 compares the sizes of alginate beads produced using needles of different sizes;

FIG. 17 compares the sizes of alginate beads produced using different airflow director sizes;

FIG. 18 shows the size distribution of alginate beads of Example 8 loaded with doxorubicin;

FIG. 19 shows the elution profile of doxorubicin from the alginate beads of Example 8;

FIGS. 20(A) and (B) are photographs of 2% High G (LB40) loaded with 59.70 mg/mL doxorubicin before lyophilisation and sterilisation under different backgrounds of light;

FIG. 21 shows photographs of 2% High G (LB40) loaded with 59.70 mg/mL doxorubicin: (A)=lyophilised beads; (B)=in PBS overnight;

FIG. 22 shows a BT4Ca Tumour in rat brain 18 days post implantation of cells;

FIG. 23 shows the results of the "shot" technique to deliver beads to the brain: Left=doxorubicin loaded beads of Example 1; Right=unloaded beads of Example 1;

FIG. 24 shows (a) tumour treated with Dox DEB after 1 day; (b) tumour treated after 5 days with Dox DEB; (c) untreated tumour control;

FIG. 25 shows tumour treated with 1 µl, 3 µl and 5 µl of Dox DEB (left to right);

FIG. 26 shows tumour treated with 1 µl, 3 µl and 5 µl of Iri DEB (left to right);

FIG. 27 is a Kaplan-Meier survival curve for rats with BT4C rat-glioma with various intratumoural treatments; and FIG. 28 shows the number of beads per 6 µl of alginate suspension in Example 15; and FIG. 29 shows the elution of Dox (10 mg/ml Dox Bead) from alginate bead suspension.

REFERENCE EXAMPLE

Outline Method for the Preparation of Microspheres

The microspheres are synthesised by the method described in WO2004/000548 as either the "low AMPS" or "high AMPS" product. Briefly, an aqueous mixture of polyvinyl alcohol macromer having acetal-linked ethylenically unsaturated groups and 2-acrylamido-2-methyl-propane sulphonate in a weight ratio of about 1:1 is suspended in a continuous phase of butyl acetate containing cellulose acetate butyrate stabiliser with agitator and is radically polymerised using redox initiation to form beads, which are washed, dyed and sieved into size fractions including the 300-500 µm, 500-700 µm and 700-900 µm fractions used in subsequent Examples. The equilibrium water content of the microspheres is 94 to 95% by weight.

Example 1a

Loading of Doxorubicin

Figure 1:
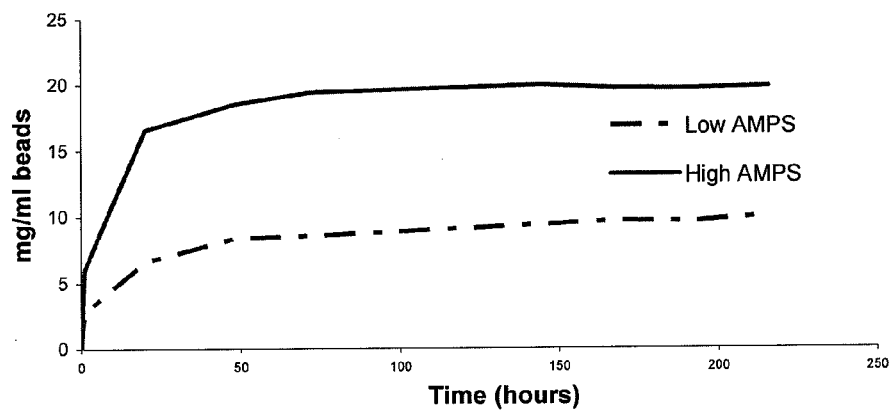

For this experiment the low AMPS microspheres prepared as in the Reference Example were used. For each size of bead used, 0.5 ml was transferred into two, 1 ml syringes, one for drug take up and the second to act as a control. The sizes chosen for the experiment were, 106-300 µm, 300-500 µm, 500-710 µm and 850-1000 µm. Additionally a further three syringes of the 500-710 µm product were prepared in order to validate the procedure. Eleven, 10 ml glass vials were covered in foil, to prevent degradation of the doxorubicin by light for the duration of the experiment. A standard curve was created. Using the 80 ml, 20 mg/ml drug solution, the following concentrations were prepared and their absorbances (at 483 nm) measured: 100 µg/ml, 50 µg/ml, 25 µg/ml, 12.5 µg/ml, 6.25 µg/ml and 3.125 µg/ml. The resulting absorbances were plotted on a graph and the equation of the line used to calculate the concentration of drug that was up-taken by the beads in the experiment. Four of the vials were filled with 5 ml of distilled water (ROMIL) to be used as controls when the beads were added. To the remaining seven vials were added 5 ml of the drug solution at the desired concentration. The starting absorbance and therefore concentration of the solution was already known from the preparation of the standard curve. In order to measure the absorbance of the 20 mg/ml solution it was necessary to dilute it 200 times, using the concentration 100 µg/ml. This 1:200 dilution was carried through for the duration of measuring the uptake of the solution by the beads. The stopwatch was started as soon as the first set of microspheres were added to the first drug containing vial, microspheres were added to each of the remaining six vials working from smallest to largest. Once sealed using the caps they were placed on the rotary mixer. The process was repeated for the control samples. The absorbances were measured in the same order as the vials were set up at time intervals of 0.167 hr (10 min), 0.5 hr, 1 hr, 2 hr, 24 hr and 96 hr. From the data the amount of drug (in mg) per 1 ml of microspheres and the % uptake of drug by 1 ml of microspheres could be calculated. The results are shown in FIG. 1.

Example 1b

Elution of Doxorubicin from Microspheres

Figure 2:
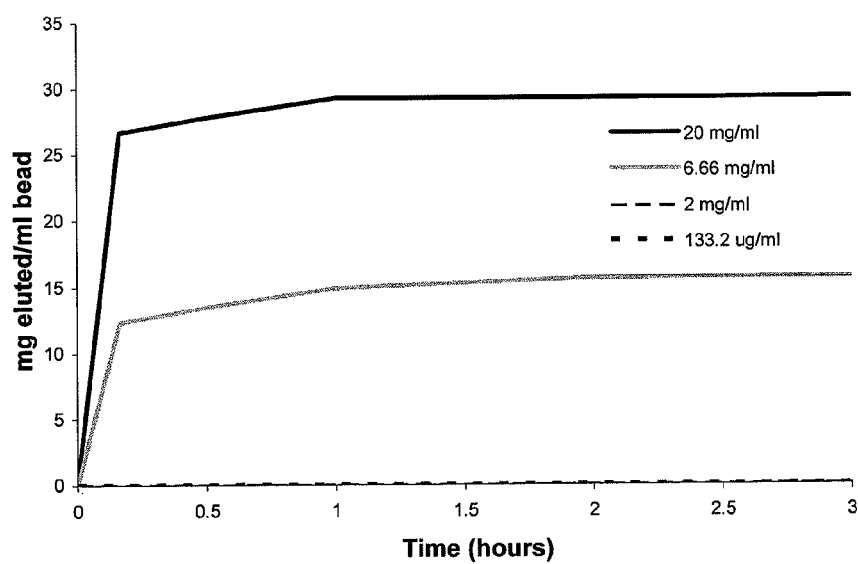
FIG. 2 shows in-vitro elution of Doxorubicin from high AMPS Bead Block.

High AMPS microspheres were loaded with various concentrations of doxorubicin and the microspheres eluted into 250 ml of distilled water (FIG. 2).

The drug eluting from the 133.2 µg/ml and 2 mg/ml loaded microspheres was still below the detection limit at 3 hours. For the higher drug loadings, a burst effect is evident in the first few minutes, followed by a prolonged period of slower release. It is surmised that the burst represents the free drug eluting from the water held within the microspheres, whereas the prolonged elution results from the drug that is "bound" into the spheres essentially by ionic interaction between the charged groups. For the highest loading of drug (from the 20 mg/ml loading solution), the burst effect represents some 45% of the total drug loading of the spheres, the remainder taking several days to completely elute from the carrier. Studies have shown that 100% of the drug is eventually eluted from the microspheres. Drug-loaded beads were lyophilised to remove water and sterilised using gamma irradiation.

Example 1c

Preloaded Product—Lyophilisation Weight Loss

Doxorubicin loaded microspheres of the present invention were subjected to lyophilisation. Percent weight loss was determined for doses of 5, 10, 20 and 45 g/ml for all of the microsphere size ranges and expressed as a % of the loaded microspheres. A consistent weight loss was obtained, indicating that any variation in the weight of loaded microspheres prior to lyophilisation had no effect on the product post lyophilisation. The data showed that there is consistently greater than 82% weight reduction on lyophilisation due to water loss.

Example 2

Preparation of Irinotecan-Loaded PVA-Hydrogel Beads (Iri DEB)

For this experiment, microspheres were prepared as detailed in the Reference Example.

Example 2a

Investigation of Microspheres Loading Capacity

Irinotecan-loading content and loading efficacy was determined using microspheres, 500-700 µm. A bead slurry was mixed with irinotecan solution (20 mg/ml) in calculated amount, rotating-mixed for at least 4 hours. The solution was measured with UV at 369 nm to determine the irinotecan concentration and the drug-loading in beads (by depletion method). Irinotecan content in beads linearly increased with loading amount under low concentration (below 50 mg/ml). Above this the loading efficacy dropped remarkably, indicating saturation of the beads.

Example 2b

Elution from Irinotecan Lyophilised Microspheres

Irinotecan was eluted from lyophilised microspheres with different loadings of camptothecin into PBS buffer. The elution rate slowed down after lyophilisation when compared with the non-lyophilised samples. Also the higher drug loading showed a slower elution compared to the lower one. Drug-loaded beads were lyophilised to removed water and sterilised using gamma irradiation.

Example 3

Comparison of Loading of Mitoxantrone with Doxorubicin and Effects on the Physical Properties of the Beads Microspheres of the invention were prepared as described in the Reference Example. Sample beads of the size range 700-900 µm were loaded by immersing the beads in aqueous solutions of Doxorubicin HCl (Dox) and Mitoxantrone 2HCl (Mitox). Loading was monitored using UV-visible spectroscopy at the respective wavelengths for absorption maxima of the two drugs (483 nm and 660 nm respectively). The beads were sized and imaged using an Olympus BX50F4 microscope with a Colorview III camcorder. Compressibility was measured using an Instron 4411 with a 50 N load cell.

The beads actively uptake both Dox and Mitox. The maximum loading capacity of Mitox is approximately half that of Dox consistent with the presence of two positively charged groups in comparison with the one of Dox (Table 1).

TABLE 1

Average maximum capacity of DEB (Drug-Eluting Bead).

| | Average (mg) of drug per mL of beads | Mols of loaded drug/ Mols of available binding sites | Standard deviation | % CV |
|---|---|---|---|---|
| Doxorubicin | 39.0 | 0.9 | 3.8 | 9.7 |
| Mitoxantrone | 20.0 | 0.5 | 0.2 | 1.0 |

CV = Coefficient of Variance.

Figure 3:
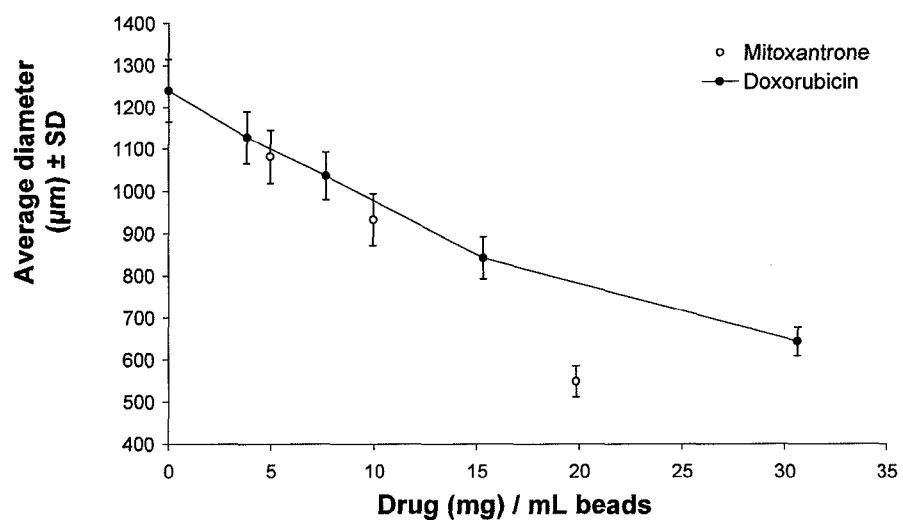
FIG. 3 shows the change in average diameter of loaded beads with increasing amount of drug (mean±sd, n=5)

For both drugs there is a size change on loading with a decrease in average diameter with increasing dose (FIG. 3). Initial size change occurs as water molecules around the ionic sulfonate groups are displaced by the more hydrophobic and bulky drugs. However, with a concentration greater than 10 mg per mL of beads, Mitox loaded beads have a lower average diameter than Dox loaded beads at the same dose. This occurs as the two binding groups of Mitox act to physically restrict the diameter of the beads, effectively cross-linking the structure.

Figure 4:
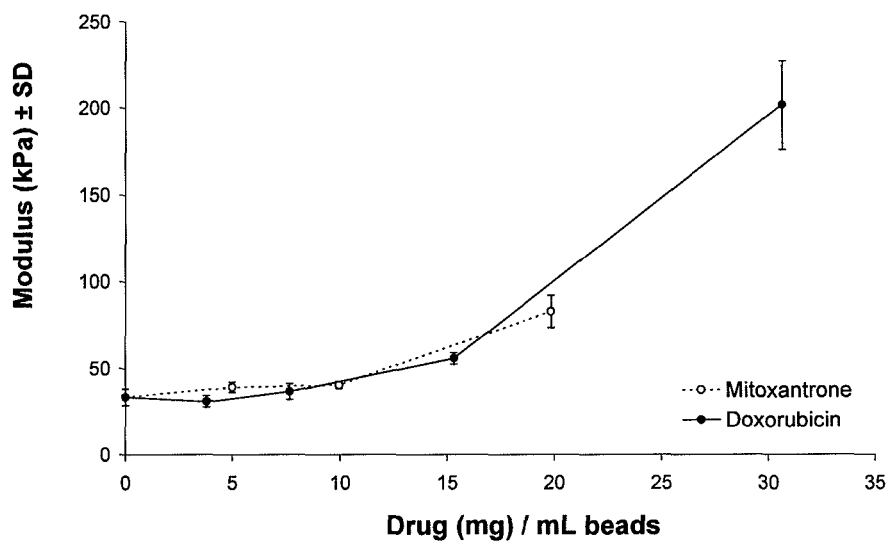
FIG. 4 shows the resistance to compression of loaded beads with increasing amount of drug (mean±sd, n=5)

Dox and Mitox loaded beads both exhibit similar resistance to compression which gradually increases with dose (FIG. 4). At concentrations approaching maximum capacity, Dox loaded beads have a significantly higher resistance to compression than unloaded beads. This is attributed to Dox's ability to self-associate through electrostatic interaction of the anthracycline aromatic rings forming dimers. At high concentrations the formation of dimers within the beads can also act to cross-link the structure. Though it is likely that Mitox can also self-associate to form dimers, the maximum loading capacity of 20 mg is not sufficient to form dimers that significantly alter the physical properties of the beads.

The maximum loading capacity of DEB using Mitox and Dox is directly controlled by the number of available charged groups. When loaded, the beads exhibit a reduction in average bead diameter and increase in resistance to compression with increasing dose. This behaviour is caused by a combination of (i) reduction in water content and (ii) cross-linking of the structure by the drug either through physical restriction by the drug itself and/or its self-association.

Loading and Elution of AQ4 and AQ4N from Beads of the Invention

Example 4

UV spectra of AQ4 and AQ4N solution

Figure 5:
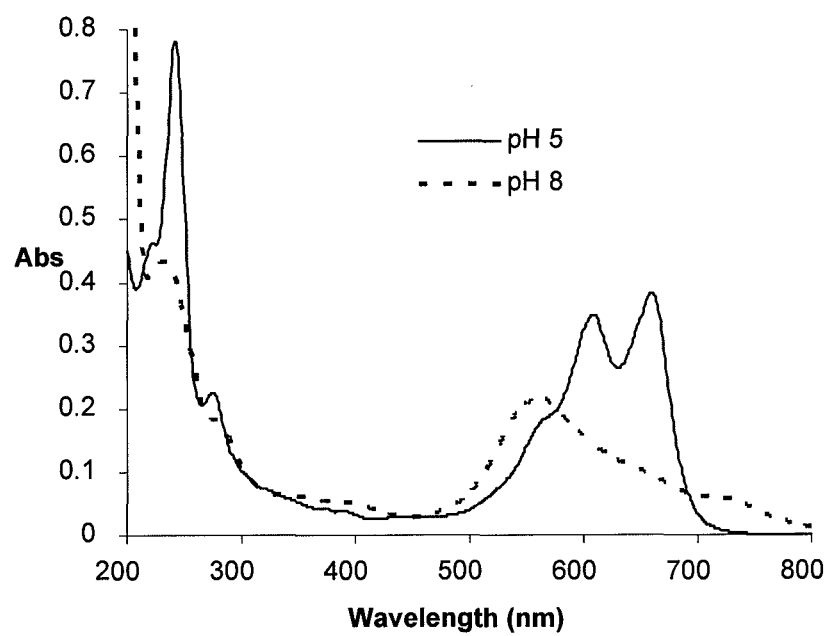
FIG. 5 is a UV scan of AQ4 at pH5 and pH8.

The AQ4 is a dark powder in appearance with low water solubility. An AQ4 aqueous solution of 5.167 mg/mL was prepared by adding an aliquot of HCl solution (1 M) to solubilise the drugs. The UV spectra of AQ4 at pH5 and pH8 are shown in FIG. 5. At low pH, in visible range there are two absorption peaks, at 608 nm and 659 nm. When pH was raised above pH6, the maximum absorption was shifted to 561 nm, due to the neutralisation of protonated tertiary amines.

Figure 6:
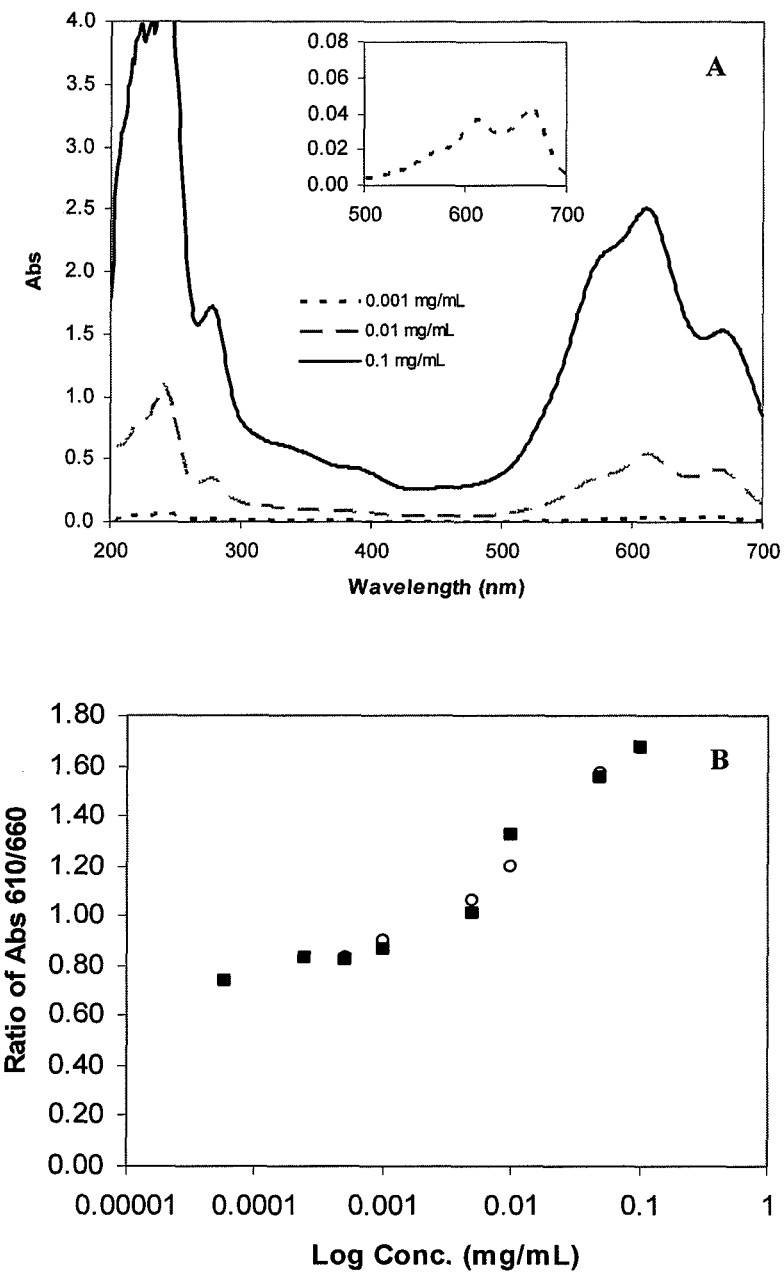
FIG. 6(A) is a UV spectrum of AQ4N at pH3.1, citrate buffer (the inserted curve is 0.001 mg/ml)
FIG. 6(B) is the ratio of Abs 610 nm/660 nm vs. AQ4N concentration.

AQ4N is a black powder, which has low water solubility. It is only soluble in water after acidification with HCl. FIG. 6A shows the UV scan of AQ4N at different concentrations in citrate buffer, pH3.1, with two absorption peaks at 610 nm and 660 nm in the visible range. In PBS buffer AQ4N shows almost the same spectrum. It is noticed that the relative absorbance of these two peaks changed with AQ4N concentration. The ratio of absorbance at 610 nm to 660 nm increased from 0.73 to 1.67 as AQ4N concentration increased from 0.000058 mg/mL to 0.1 mg/mL (FIG. 6B). This suggests a possible aggregation of drug molecules in solution with concentration increase at about 0.002 mg/mL.

A standard curve of AQ4 in aqueous solution can be constructed, which gives the relationship of drug concentration and absorbance:

Concentration of AQ4=Abs.@660 nm×0.0245.

Standard curves of AQ4N were also constructed into media, citrate buffer (pH3.1) and PBS (pH 7.4). The two curves basically overlap each other, suggesting weak effect of media in these cases. The relationship of drug concentration and absorbance at 610 nm are:

Concentration of AQ4N=0.0007×Abs$^3$+0.004×Abs$^2$+ 0.0296×Abs (citrate buffer).

Concentration of AQ4N=0.0056×Abs$^3$−0.0067×Abs$^2$+ 0.0345×Abs (PBS).

Example 5

Morphology and size distribution of AQ4 and AQ4N-loaded DC Bead

Figure 7:
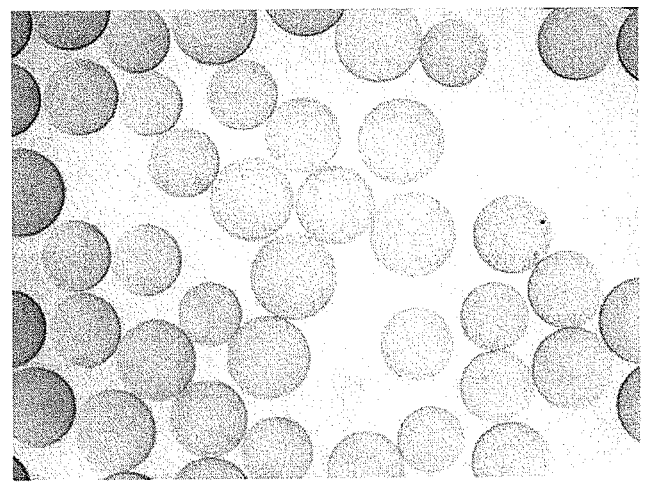
FIG. 7 is a photograph of DC Bead (500-700 μm) without drug loading.
Figure 8:
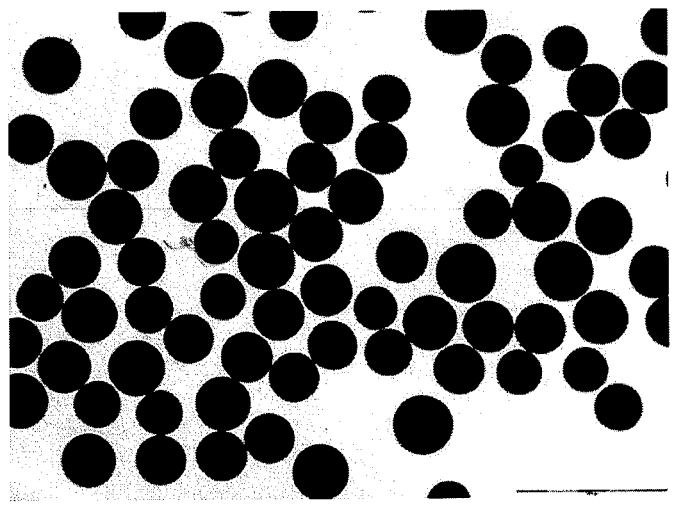
FIG. 8 shows the appearance of AQ4-loaded DC Bead (20 mg/ml)
Figure 9:
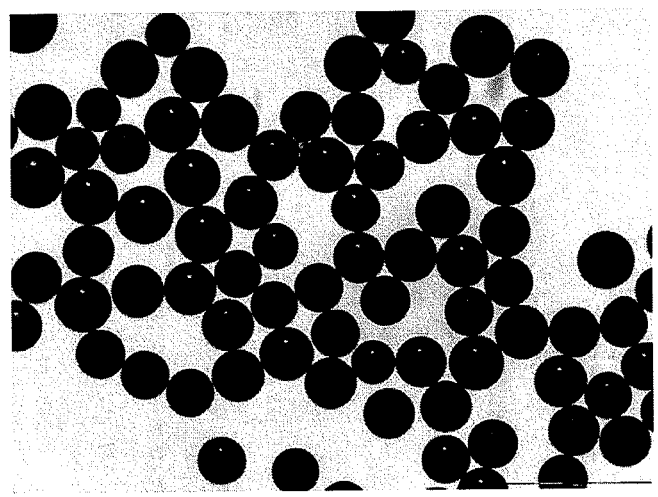
FIG. 9 shows the appearance of AQ4N-loaded DC Bead (20 mg/ml)
Figure 10:
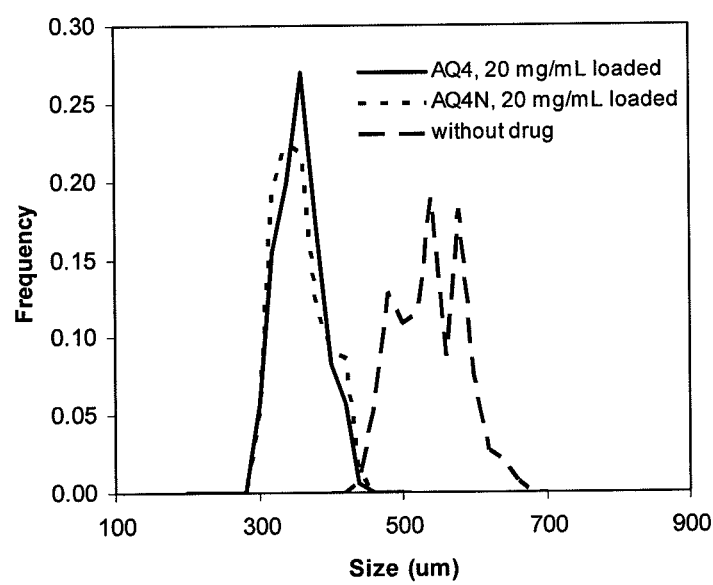
FIG. 10 shows the size distribution of DC Bead with and without AQ4 loading.

DC Bead for embolisation chemotherapy is mainly composed of PVA hydrogel with AMPS group (2-acrylamido-2-methylpropane sulfonate sodium salt) and tinted with blue dye (FIG. 7). After loaded with AQ4, the DC Bead became black and nontransparent from the original transparent DC Bead as shown in FIG. 8. FIG. 9 shows the AQ4N-loaded DC Bead with black colour, which also indicates a high drug loading. From the two photos, these two drug-loaded beads keep their spherical shape. The change of size distribution of DC Bead with and without AQ4 and AQ4N loading is show in FIG. 10. The size of the loaded beads tend to decrease due to the increased hydrophobicity of the beads, which in turn expel water molecules out of the beads. Table 1 gives the parameters of the DC Bead size change. From the table, the mean size (~346 μm), maximum and minimum size of AQ4- and AQ4N-loaded beads are almost the same. Compared to the DC Bead without drug the mean size decreases about 180 μm.

TABLE 2

Size of DC Bead with and without AQ4 loading

|  | Maximum size (μm) | Minimum size (μm) | Mean (μm) | SD |
|---|---|---|---|---|
| AQ4 loaded DC Bead | 423 | 287 | 347 | 31.1 |
| AQ4N loaded DC Bead | 427 | 282 | 346 | 33.9 |
| DC Bead | 641 | 431 | 530 | 46.6 |

Example 6

AQ4 and AQ4N Loading Profile

Protonated AQ4 and AQ4N can be loaded into DC Bead which carries negatively charged sulfonate groups through the interaction of static electricity charge. This ion-exchange mechanism has been proven by the fact that no drug elution was observed when loaded beads were placed in water, and in contrast, the drug was released either in saline or in PBS buffer.

Figure 11:
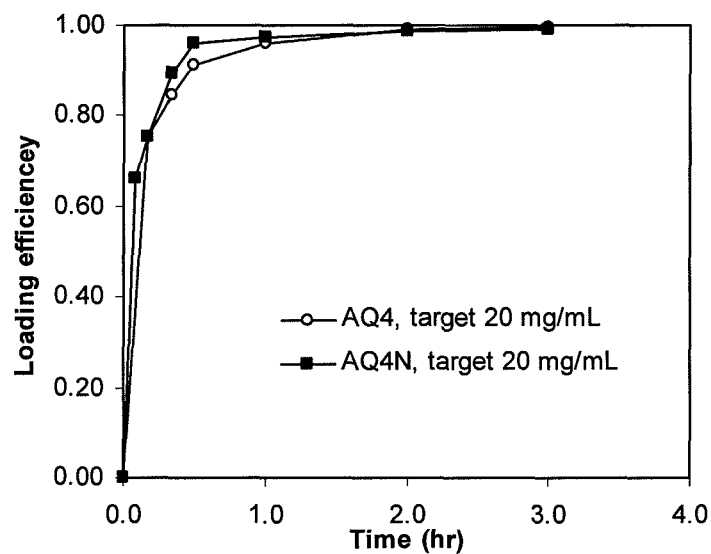
FIG. 11 shows the AQ4 and AQ4N loading profile of DC Bead (500-700 µm)

FIG. 11 shows the profile of loading 20 mg AQ4 and AQ4N into 1 mL DC Bead (500-700 μm). Target loading was 20 mg/ml (at room temperature). The loading rates of these two drugs are very fast. Within first 10 minutes, about 75% of AQ4 and AQ4N have been loaded. After 3 hours, the loading efficiency was above 99%.

The maximum loading capacity of DC Bead, 500-700 μm, was studied by mixing 0.5 mL DC Bead with AQ4N solution (target loading 60 mg/mL) over a 20 hr period. The measured maximum loading capacity of AQ4N in DC Bead is 26.9 mg/mL. The value is lower than the loading capacity of doxorubicin in DC Bead (40 mg/mL), due to the double charge of AQ4N compared to the single charge of doxorubicin. In theory each doxorubicin combines one sulfonate group, hence, AQ4N with two charges is expected to bind two sulfonate groups.

The experiment on loading capacity of AQ4N in DC Bead suggests that a maximum about 26×4=104 mg of AQ4N could be delivered into a tumour by a typical TACE (Transarterial Chemembolisation) with 4 mL loaded DC Bead.

Example 7

Elution Experiment

Figure 12:
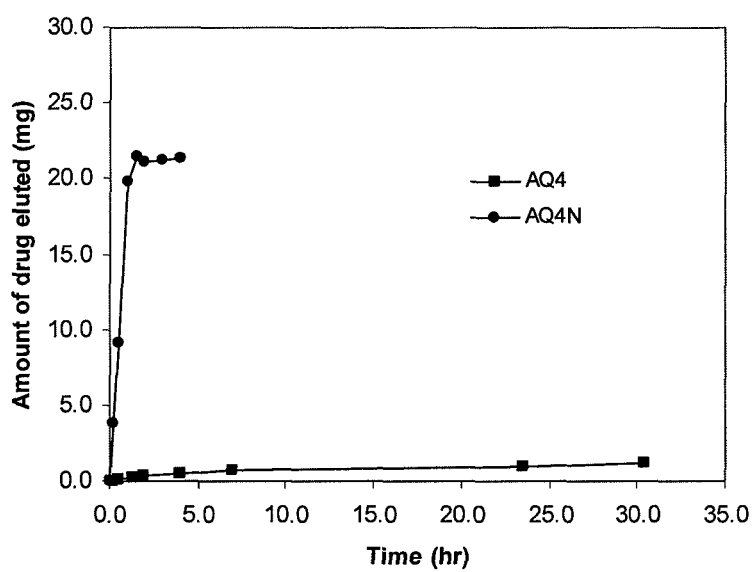
FIG. 12 shows the AQ4 and AQ4N elution from DC Bead to 200 mL PBS at room temperature.

FIG. 12 shows the elution profile of AQ4 and AQ4N by mixing drug-loaded DC Bead with PBS. The target loading was 20 mg/ml. In this procedure, 1 mL AQ4-loaded DC Bead with 20 mg/mL AQ4 or AQ4N were mixed with 200 mL PBS and roller-mixed at room temperature. At certain time point samples were collected to measure UV absorbance. FIG. 12 shows two very different elution profiles, in which the AQ4 elution is a slow procedure, only 1.18 mg (6% of total loading) of AQ4 was eluted after 30 hr in PBS. However, the AQ4N shows a very fast elution, in which 19.8 mg AQ4N was eluted after 1 hr mixing with PBS.

The AQ4 molecule has four nitrogens that can be protonated with acid and provide strong binding forces with sulfonate groups within DC Bead. In AQ4N, there are two nitrogens which can be protonated. The positive charge from protonated nitrogen could be easily delocalised by the neighbouring benzene ring. Therefore, the interaction between the sulfonate group and AQ4N can be much weakened, and results in a fast elution of the drug from loaded beads.

Figure 13:
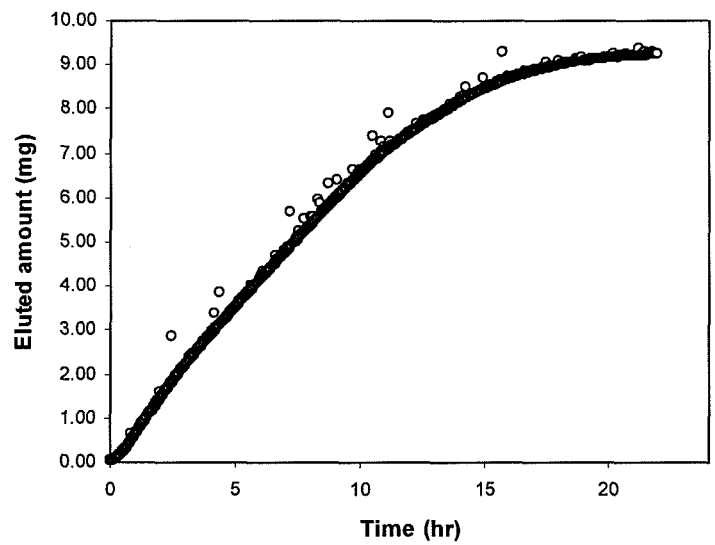
FIG. 13 shows the AQ4N elution from DC Bead (0.5 mL beads with 20 mg/ml loading) to PBS, tested by T-apparatus at 37° C.

T-apparatus was designed to simulate the drug elution from embolisation beads in vivo, in which the beads are restricted and stacked in a very narrow area of blood vessel. Hence, the drug elution rate was significantly reduced. FIG. 13 shows the AQ4N elution profile from the drug-loaded DC Bead. In this experiment, 0.5 mL DC Bead with 10 mg AQ4N was placed into 300 mL PBS buffer, 37° C. The AQ4N elution was monitored at 610 nm. From the curve, there was no burst of drug in the beginning, and about 90% of drug was eluted after 20 hr. This elution profile demonstrates that the AQ4N could be eluted from DC Bead consistently in vivo.

AQ4 and AQ4N can be loaded into DC Bead with relative ease. The maximum loading capacity of AQ4N in DC Bead is 26 mg/mL beads. The drug-loaded DC Beads retain the spherical shape with an intense black colour, with a decreased size compared to the beads without drug loading. The size distribution of loaded beads is the same as the original DC Bead. AQ4 elution from DC Bead to PBS is very slow because of the strong interaction between the cationically-charged groups of the drug and sulfonate groups of the polymer beads. AQ4N elution is relatively faster as the interaction is reliant upon the mildly cationic secondary amine groups. The T-apparatus experiment more closely emulates the in vivo situation with diffusion and convection components of the release process. This demonstrates that AQ4N can be eluted from DC Bead consistently over about 20 hr period, providing a therapeutically meaningful sustained release.

Example 8

Preparation of Alginate Microspheres

Alginate microspheres were prepared from super-pure alginate with either High G or High M content by extrusion of an alginate solution of specific concentration into a gelling bath of calcium or barium ions (usually 20 mM) as described in below.

Example 8a

Manufacture of Alginate Beads Using the an Air-Knife Extrusion Method

Sodium alginate solution (alginate concentration=0.6%) and barium chloride solution (concentration=290 mM) were made in ultra-pure water. The needle of the machine used to manufacture alginate beads was washed with saline prior to use. Under a constant air pressure (P=1 bar), approximately 2 mL of alginate solution was injected through the needle of the air-knife extrusion machine using a 3 mL syringe into 10 mL of barium chloride solution contained in a plastic petridish, where it was left to crosslink for about 20 minutes. After crosslinking, the resultant beads were washed with saline three times through a filter (100 μm) to eliminate the excess barium solution and the beads with extremely small sizes. The components assembled onto the base (including the Base, Needle, Jet and Airflow director, etc.) were washed with saline, EDTA and deionised water after each use.

Example 8b

Alginate Beads Manufactured Under Different Injection Rates (Airflow rate—4 L/min, needle size—0.7 mm, size of airflow director—2.5 mm)

TABLE 3

Size comparison under different injection rates

| | Max (μm) | Min (μm) | Mean (μm) | Stdev. |
|---|---|---|---|---|
| 5 mL/min | 382 | 276 | 331 | 19 |
| 10 mL/min | 410 | 199 | 326 | 29 |
| 20 mL/min | 448 | 265 | 358 | 33 |
| 30 mL/min | 524 | 310 | 394 | 37 |

It can be observed from FIG. 14 and Table 3 that there is a gradual increase in the sizes of alginate beads when increasing the injection rate from 5 to 30 mL/min. However, increasing injection rate does not have a significant influence on the sizes of alginate beads since the majority of the beads are in the range of 300~500 μm. The majority of beads under each condition all have uniform sizes and shapes. Most of the beads have very smooth surfaces regardless to the injection rate used.

Example 8c

Alginate Beads Made Under Different Airflow Rates (Injection rate—10 mL/min, needle size—0.7 mm, size of airflow director—2.5 mm)

TABLE 4

Size comparison under different airflow rates

| | Max (μm) | Min (μm) | Mean (μm) | Stdev. |
|---|---|---|---|---|
| 2 L/min | 1054 | 913 | 975 | 27 |
| 4 L/min | 335 | 238 | 299 | 19 |
| 6 L/min | 259 | 82 | 154 | 38 |

According to Table 4 and FIG. 15 the correlation between the sizes of beads and airflow rate is reversely-proportional, as the size of alginate beads increases dramatically when reducing the airflow rate, especially from 4 to 2 L/min. At some point in between 2 and 4 L/min, there would appear to be a flow rate barrier below which the beads are very big.

The bigger beads manufactured under 2 L/min Airflow rate have a better uniformity in terms of their sizes and shapes comparing to those produced with 4 and 6 L/min Airflow rate. There are many very small beads (<100 μm), observed in the picture at 6 L/min. They were not filtered out since they were smaller than the filter range. Despite the size differences, the majority of the beads have very good quality with respect to morphology.

Example 8d

Alginate Beads Manufactured Under Different Needle Sizes (Airflow rate—4 L/min, injection rate—10 mL/min, size of airflow director—2.5 mm)

TABLE 5

Size comparison under different needle sizes

| | Max (μm) | Min (μm) | Mean (μm) | Stdev. |
|---|---|---|---|---|
| d = 0.7 mm | 410 | 199 | 326 | 29 |
| d = 1.0 mm | 545 | 347 | 485 | 27 |

As observed in Table 5 and FIG. 16, the alginate beads produced using a needle size of 1.0 mm are bigger than those made with a needle size of 0.7 mm.

Changing needle size does not bring any significant difference in terms of bead morphology since both kinds of beads have very round shape and smooth surface.

Example 8e

Alginate Beads Made Under Different Airflow Directors (Airflow rate—4 L/min. injection rate—10 mL/min, needle size—0.7 mm)

TABLE 6

Size comparison under different airflow directors

|  | Max (µm) | Min (µm) | Mean (µm) | Stdev. |
|---|---|---|---|---|
| d = 2.0 mm | 399 | 107 | 259 | 67 |
| d = 2.5 mm | 410 | 199 | 326 | 29 |

It is natural to think that the wider the airflow director, the bigger the beads produced. This is supported by the data provided in Table 6, where the average size of beads made by an airflow director of 2.5 mm is about 70 µm bigger than the average size of those made by airflow director of 2.0 mm. According to FIG. 17, it is seen that the beads made by an airflow director of 2.0 mm are distributed across a much wider size range: 100~400 µm, whereas the majority of those made under an airflow director of 2.5 mm are in the range of 260~40 µm. The alginate beads made with an airflow director of 2.5 mm are more uniform than the beads made with an airflow director of 2.0 mm in terms of their shapes and sizes. Another difference between these two types of beads is the morphology. The beads produced under an airflow director of 2.5 mm seem comparatively smoother than those produced under airflow director-2.0 mm.

Summary of the Effects Different Parameters have on Alginate Beads Formation

The sizes of alginate beads can be modified by altering each of the above experimental parameters, but modifying the airflow rate causes the most significant impact on size.

Example 9

Loading of Alginate Microspheres with Doxorubicin

Loading capacity test: 0.2 mL of 2% and 0.3 mL of 0.6% of alginate beads (avg 200 µm diameter) were measured by use of a 2 mL pipette. Ringer solution (NaCl 8.6 g, KCl 0.3 g, $CaCl_2 \cdot 2H_2O$ 0.437 g in 1 L deionised water) was added to facilitate the measurement and bead transfer. The packing solution was subsequently removed using a glass pipette with a cotton filter at its tip.

1.39 mL of 10.07 mg/mL doxorubicin hydrochloride aqueous solution was mixed with the alginate beads at target loading of 70 mg/mL for 2% beads and 47 mg/mL for 0.6% beads, respectively. The mixtures were subsequently shaken on a IKA KS 260 basic shaker overnight at a motor speed 150/min. The loading solution was then diluted 50 times and measured by UV spectroscopy at 483 nm to determine the concentration of doxorubicin residue in solution.

The measured loading capacity of the alginate beads is given in Table 7. It appears to follow a logical trend that the beads with higher alginate concentration load more doxorubicin because of the higher guluronic(G)/mannuronic(M) acid content, and hence increased number of anionic binding sites for the drug. From the data it is also clear that for the same alginate concentration, High G beads have higher loading capacity compared to the High M beads.

TABLE 7

Loading capacity of Alginate Beads of Example 8

| Batch No. | Composition and G/M content | Loading capacity (mg/mL) | Standard deviation (SD) (mg/mL) |
|---|---|---|---|
| LB40 | 2% High G | 59.70 | 0.27 |
| LB43 | 0.6% High G | 36.79 | 1.13 |
| LB42 | 2% High M | 51.73 | 1.55 |
| LB41 | 0.6% High M | 25.64 | 0.82 |

The size distribution of alginate beads of Example 8 loaded with doxorubicin are shown in FIG. 18. The corresponding parameters, including unloaded bead data are listed in Table 8. Generally, the beads maintained their narrow size distribution after drug loading. However, the size is seen to decrease with doxorubicin loading due to the increased hydrophobicity of the drug-loaded beads. The size of High G beads is reduced less compared to the High M counterparts at the same alginate concentration. Here the greater stiffness of higher cross-linked High G beads plays a major role in the resistance to shrinkage, although the High G beads tend to hold more drug (Table 7).

In Table 8, the size of drug-loaded beads with low alginate concentration (0.6%) decreased much more than the high alginate concentration (2%). Under the same bead volume, the low polymer content within the beads led to a greater decrease in volume after drug loading, meaning that more water was expelled from the beads. The structure collapse caused by the lack of polymer content can cause a deformed spherical shape.

TABLE 8

Comparison of alginate beads of Example 8 with/without doxorubicin

| Batch No. | Composition & G/M content | $Size_{mean}$ without Dox (µm) | SD (µm) | $Size_{max}$ (µm) | $Size_{min}$ (µm) | $Size_{mean}$ (µm) | SD (µm) | Size decrease after loading (%) |
|---|---|---|---|---|---|---|---|---|
| LB40 | 2% High G | 215 | 3 | 201 | 162 | 179 | 6 | 16.7 |
| LB43 | 0.6% High G | 182 | 4 | 187 | 112 | 140 | 7 | 22.9 |
| LB42 | 2% High M | 192 | 5 | 179 | 117 | 152 | 9 | 20.8 |
| LB41 | 0.6% High M | 216 | 4 | 184 | 114 | 156 | 10 | 28.1 |

Example 10

Elution of Doxorubicin from Alginate Microspheres

FIG. 19 shows the elution profile of doxorubicin from alginate beads of Example 8. FIG. 19(A) shows from 2% High G/M beads; (B) shows from 0.6% High G/M beads. The elution conditions were 0.2 mL 2% High G/M beads, 0.3 mL 0.6% High G/M beads, 200 mL PBS (fresh PBS was added after solution withdrawn), ambient temperature, roller-mixer. The elution from high loading beads (FIG. 19A) tends to be slower compared to the elution from low loading shown in FIG. 19B. Meanwhile, the elution rates of doxorubicin from 2% High G/M beads are almost the same. In FIG. 19B, the elution from 0.5% High M beads is slightly faster than that from High G beads.

In this study 0.2 or 0.3 mL of alginate beads was used for elution test, and close to sink conditions were maintained by replenishment with fresh PBS. Therefore, the elution rate was relatively fast. It was found that the rate of elution depended not only on the structure of beads and drug amount, but also on the volume ratio of beads vs elution medium. The last factor is characteristic of ion-exchange type mechanism of drug elution, which means that the ion concentration provided from the medium must be high enough or at least equal to the drug in beads for exchange.

Example 11

Figure 20:
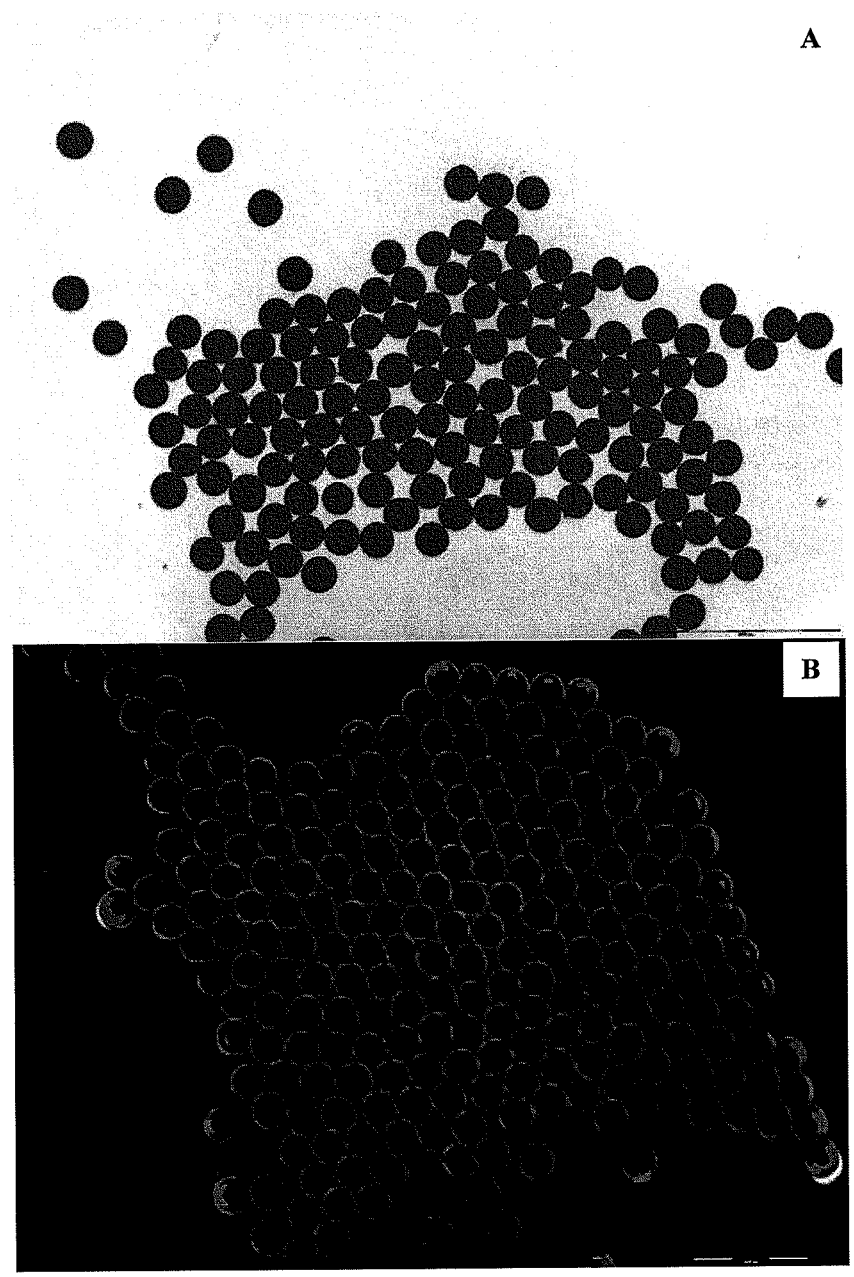

Imaging of Doxorubicin Loaded Alginate Beads Post Lyophilisation and Sterilisation Alginate beads of 2% High G content were seen to produce the best quality beads post lyophilisation and gamma irradiation (FIGS. 20 and 21). The scale bar on FIG. 20 is 1000 µm and is 200 µm on FIG. 21.

Example 12

Implantation of Drug Loaded Beads in a Rat Tumour Model

The rat glioma cell line (BT4C) has been characterized as a glial tumour with histopathological appearance of a gliosarcoma. The cell line was obtained from Institute for Cell Biology, University Essen, Hufelandstr. 55, 45122 Essen. The glioma cell line was maintained in culture in DMEM media in an incubator with 5% $CO_2$ at 37° C. Flasks were kept in the logarithmic growth phase and cells were passaged every 3-4 days.

Rats were anaesthetised using ketamine and medetomide. Their heads were shaved and disinfected. After a midline scalp incision, a 3-mm burr hole was made into the forebrain. The animals were then placed in a stereotactic frame, and 8000 glioma cells were implanted. After ensuring hemostasis, the wound was closed with surgical sutures. FIG. 22 demonstrates the massive tumour that is typically obtained some 18-23 days post implantation of the cells (which would cause death of the animal).

Bead implantations were performed typically 1 week post cell implantation via the same hole. The beads were implanted using a "shot" technique in which the entire volume was injected by a sharp injection of the syringe (FIG. 23). The left side of FIG. 23 shows the Doxorubicin loaded beads of Example 1, and the right side the unloaded beads of Example 1. It was found that slower administration caused expulsion of the beads from the tissue. Non-drug loaded PVA hydrogel beads were seen to be tolerated extremely well in the brain tissue with no adverse reactions.

The study determined the toxicity of treatment on healthy rats at different doses of drug loaded bead. There were 3 groups of animals, as shown in Table 9. In the test groups, 3 doses of bead/drug were tested. Rats were randomly assigned to a group. Each group had 6 rats, with 6 rats at each dose level tested.

TABLE 9

Groups Evaluated in the Rat Tumour Model

| Volume of beads injected | Group | | |
| --- | --- | --- | --- |
| | 1 Unloaded PVA beads | 2 Dox DEB | 3 Iri DEB |
| 1 µL n = 6/group | X | X | X |
| 3 µL n = 6/group | — | X | X |
| 5 µL n = 6/group | — | X | X |

The day of treatment is designated as Day 0.

FIG. 24 shows histological sections of tumours with and without treatment with high dose Dox DEB. One day after treatment (a) the tumour appeared bright, indicating regressive tissue changes. No significant adverse effects were seen, with no brain edema and no inflammatory reaction. The small arrows indicate the position of the Dox DEB in the tumour. At day 5 (b) the tumour has become necrotic with some evidence of peritumoural inflammation probably caused as a consequence of the necrosis. The adjacent brain tissue remained unaffected. Section (c) shows an untreated control tumour with dark blue staining of the tumour cells indicating large numbers of cell nuclei and dividing cells.

FIG. 25 shows the results from the dose-finding study using 1-5 µL injections of Dox DEB. This shows that just 1 µL of Dox DEB administered by the shot technique appears a reasonable volume for affecting tumour necrosis whilst avoiding the toxic side effects of the blood pooling in the tissue evident with 5 µL.

FIG. 26 shows a similar dose-finding study using Iri DEB and in this case, all doses were well-tolerated with no signs of hematoma and a dose-dependent necrosis, although not as widely spread efficacious as Dox DEB.

When the animals were assessed by survival analysis, a Kalplan-Meier curve was constructed (FIG. 27) which shows the Dox DEB to significantly extend the survival of rats treated with the 1 µL dose, with a doubling of survival time.

Some 16 days after treatment with Dox DEB, a native histological section and its corresponding section were viewed under fluorescent microscopy. This clearly demonstrated elution of the drug from the beads and into the parenchyma after injection into the rat glioma, as the doxorubicin was seen to fluoresce red under excitation. It also demonstrated that some drug still remains in some beads at this time point.

These results confirm that drug eluting beads should be clinically effective for the treatment of glioma and offer a new therapeutic armamentarium complementary to current treatment methods such as surgery and implantation of radioactive seeds.

Example 13

Alginate-Bead Suspensions for Stereotactic Injection

A vial of lyophilised doxorubicin-loaded high-AMPS beads (25 mg dox/mL beads, 2 mL original volume) was rehydrated in 2 mL water for injection. 2 ml of alginate solution (high viscosity, high M rich ultrapure alginate, CellMed) was added directly to this vial and mixed for 10 s using a vortexer. 6 μL of the resulting suspension was aspired into a 50 μL Hamilton syringe, which was completely pre-filled with alginate solution alone.

The total volume of a Hamilton syringe is made up of the volume of the glass cylinder and the volume of the injection needle. The cylinder contains 50 μL and an additional ~28 μL in the 19 G needle. For the filling procedure, the glass cylinder of the syringe and the needle were firstly filled completely with alginate solution. Then 6 μL were pushed out and subsequently 6 μL of alginate-bead suspension were drawn into the syringe. In this way a volume of 6 μL of alginate-bead suspension was positioned at the tip of the syringe needle.

Example 14

Stereotactic Injection of the Alginate-Bead Suspension

For injection into the rat, the needle was inserted into the brain at the calculated coordinates and a volume of 7 μL was injected as fast as possible ("shot injection"). Then the syringe was retracted 2 mm and 3 μL of alginate were additionally injected for sealing of the injection canal. The needle was left in this position for 15 minutes for termination of the gelation process.

Example 15

Injectability of the Alginate-Bead Suspension (In Vitro Findings)

Using the above described mixing protocol for animal experiments the injectability was tested for the unloaded High AMPS beads, and beads loaded with Irinotecan and Doxorubicin. Independent of whether the beads were loaded with drugs, it was easy to achieve a complete evacuation of the syringes. In this respect mixing of the beads with alginate is an improvement in comparison to the usage of beads and particularly Doxorubicin beads alone. To have an estimate of the number of beads per injection volume of 6 μL, syringes were filled with unloaded beads and with beads loaded with Irinotecan and Doxorubicin (0.5, 1 and 10 mg). The syringe content was then squirted onto glass slides, and the total number of beads was counted. The results are given in FIG. 28. The highest number of beads is found in the unloaded bead group and the lowest in the Dox10 group. Differences between the groups were all significant, except for Dox10 vs. Dox1 (ANOVA, Tukey's multiple comparison test).

Example 16

Calculation of Drug Dosages Per 6 μL Injection Volume

Based on the above described mixing protocol the resulting drug dosage was calculated for an injection volume of 6 μL (Table 10).

TABLE 10

| | Dose calculations | | | |
|---|---|---|---|---|
| | Doxorubicin | | Irinotecan | |
| | previous experiments | current study (modified mixing protocol) | previous experiments | current study (modified mixing protocol) |
| Drug dose per volume beads [mg/vial] | 37.5 | 10<br>1<br>0.5 | 42 | 100 |
| Concentration [mg/μl susp. or mix] | 0.0375 | 0.0025<br>0.00025<br>0.000125 | 0.14 | 0.025 |
| Dose per animal [mg] | 0.0375 | 0.015<br>0.0015<br>0.00075 | 0.14 | 0.15 |

Example 17

Injectability—Morphological Findings after Cerebral Injection

Exploratory animal experiments were performed to examine the distribution of beads and the in vivo toxicity within brain tissue after intracerebral injection of alginate-bead suspensions.

Tissue Distribution:

The animals were injected with 6 μL beads alginate suspension with an additional injection of 4 μL alginate as described above. Waiting 15 minutes after injection of the alginate before retraction of the needle resulted in gellation of the alginate suspension and no relevant reflux of either beads or alginate was observed.

Microphotographs of rats implanted with unloaded beads, and Doxorubicin- or Irinotecan loaded beads were taken. Animals were fixated immediately after the implantation procedure. Minor bleeding along the injection canal was found, but no major tissue damage. Corresponding to the in vitro estimation of particle number per injection volume, the greatest number of implanted beads was found with unloaded beads, the lowest with Doxorubicin loaded beads.

Example 18

Toxicity Experiments with Alginate-Bead Suspensions

6 μL of Doxorubicin or Irinotecan alginate suspension (plus 4 μL for sealing the injection canal) were injected into healthy rats. The brains were investigated histologically 6 days later. Injection into healthy brain tissue revealed a cylindrical distribution of the beads along the injection canal. 6 days after implantation a compact bead deposit surrounded by low- to mid-grade brain tissue necrosis and scarce hemorrhages could be seen.

Example 19

Exploratory Efficacy Experiments 6 animals were inoculated with tumour cells. 5 days later three of them were injected with unloaded beads and the remaining three animals with Dox10 Beads. The brains were histologically examined 6 days later. The animals showed no significant impairment of their general condition nor any neurological deficits during the experiment. The histological findings indicate the efficacy of Doxorubicin and Irinotecan alginate suspension similar to the results after injection of non-suspended beads. The extent of haemorrhages caused by doxorubicin appeared acceptable. In the micrograph of the brain implanted with unloaded beads, a compact beads deposit was surrounded by developing tumour tissue. In the micrograph of the brain implanted with Dox10 beads, the internal tumour structure is destroyed, and a larger necrosis area and some tumour hemorrhages could be seen.

The mixing procedure and implantation procedure creates reproducible bead deposits within healthy brain and tumor tissue. The alginate-bead formulation facilitates the injection. Alginate gellation prevents the reflux of beads out of the injection canal. The application technique is considered reproducible and efficient.

Example 20

Elution of Dox from an alginate-bead suspension in vitro 1 mL of lyophilized Dox beads (10 mg Dox/mL beads) were hydrated in water as described in Example 13. The beads were suspended in alginate solution and water added if required in order to make the final required concentration of alginate (0.5, 1 or 1.5 wt %). Drug elution was measured by injecting the alginate-bead suspension into a bottle containing 400 mL of Ringers solution in order to gel the alginate and provide ions for elution of the drug. The solution was sampled periodically and the drug concentration determined using UV-Visible spectroscopy at 483 nm. FIG. 29 shows the elution profiles and shows that there is some retardation of Dox release over the first 24 hrs when in alginate suspension. The concentration of the alginate seems to have little effect.

The invention claimed is:

1. A method of treatment of a brain tumor comprising introducing into the brain a composition comprising microspheres, wherein the microspheres comprise a water-insoluble, water-swellable, non-biodegradable, biocompatible polymer which is anionically charged at pH7, and electrostatically associated with the polymer, in releasable form, a cationically charged chemotherapeutic agent, wherein in the treatment the chemotherapeutic agent is released from the microspheres; and wherein when equilibrated in water at 37° C., the microspheres comprise at least 40 wt % water based on weight of polymer plus water and have diameters in the range of 50 to 500 μm, wherein the composition additionally comprises a viscosity modifier which gels after administration into the brain and increases the viscosity of the composition, the viscosity modifier comprising alginate, and in the treatment, the composition is injected into the brain.

2. The method according to claim 1, wherein the chemotherapeutic agent is an anthracycline compound.

3. The method according to claim 2, wherein the anthracycline compound is Doxorubicin.

4. The method according to claim 1, wherein the chemotherapeutic agent is Irinotecan.

5. The method according to claim 1, wherein the chemotherapeutic agent is a camptothecin compound.

6. The method according to claim 1, in which the polymer is polyvinyl alcohol.

7. The method according to claim 6, in which the polymer is formed from polyvinyl alcohol (PVA) macromer, having more than one ethylenically unsaturated pendant group per molecule, by radical polymerization of the ethylenic groups.

8. The method according to claim 7, in which the PVA macromers are copolymerized with ethylenically unsaturated monomer.

9. The method according to claim 8, in which the monomer includes ionic monomer having the general formula I $$Y^1BQ^1$$

in which $Y^1$ is selected from

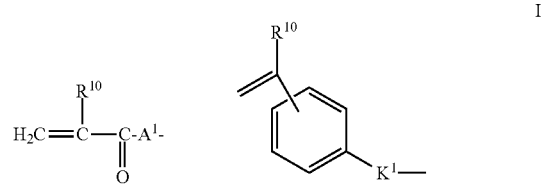

$CH_2$=$C(R^{10})$—$CH_2$—O—, $CH_2$=$C(R^{10})$—$CH_2OC(O)$—, $CH_2$=$C(R^{10})OC(O)$—, $CH_2$=$C(R^{10})$—O—, $CH_2$=$C(R^{10})CH_2OC(O)N(R^{11})$—,
$R^{12}OOCCR^{10}$=$CR^{10}C(O)$—O—, $R^{10}CH$=$CHC(O)$O—, $R^{10}CH$=$C(COOR^{12})CH_2$—$C(O)$—O—,

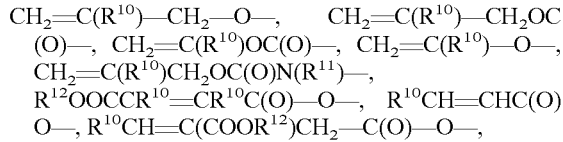

wherein:
$R^{10}$ is hydrogen or a $C_1$-$C_4$ alkyl group;
$R^{11}$ is hydrogen or a $C_1$-$C_4$ alkyl group;
$R^{12}$ is hydrogen or a $C_{1-4}$ alkyl group or $BQ^1$ where B and $Q^1$ are as defined below;
$A^1$ is —O— or —$NR^{11}$—;
$K^1$ is a group —$(CH_2)_rOC(O)$—, —$(CH_2)_rC(O)O$—, —$(CH_2)_rOC(O)O$—, —$(CH_2)_rNR^{13}$—, —$(CH_2)_rNR^{13}C(O)$—, —$(CH_2)_rC(O)NR^{13}$—, —$(CH_2)_rNR^{13}C(O)O$—, —$(CH_2)_rOC(O)NR^{13}$—, —$(CH_2)_rNR^{13}C(O)NR^{13}$— (in which the groups $R^{13}$ are the same or different), —$(CH_2)_rO$—, —$(CH_2)_rSO_3$—, or, optionally in combination with B, a valence bond and r is from 1 to 12 and $R^{13}$ is hydrogen or a $C_1$-$C_4$ alkyl group;
B is a straight or branched alkanediyl, oxaalkylene, alkanediyloxaalkanediyl, or alkanediyloligo(oxaalkanediyl) chain optionally containing one or more fluorine atoms up to and including perfluorinated chains or, if $Q^1$ or $Y^1$ contains a terminal carbon atom bonded to B a valence bond; and
$Q^1$ is an anionic group.

10. The method according to claim 9, in which $Q^1$ is a carboxylate, carbonate, sulphonate, sulphate, nitrate, phosphonate or phosphate group.

11. The method according to claim 9, in which $Y^1$ is a group $CH_2=CR^{10}COA^1$- in which $R^{10}$ is H or methyl and in which $A^1$ is NH and B is an alkanediyl group of 2 to 6 carbon atoms.

12. The method according to claim 11, wherein $R^{10}$ is methyl.

13. The method according to claim 6, wherein the PVA monomer has an average molecular weight in the range 1000 to 500,000 D.

14. The method according to claim 13, wherein the PVA monomer has an average molecular weight in the range 10,000 to 100,000 D.

15. The method according to claim 7, in which the pendant ethylenic groups are linked via cyclic acetal linkages with oxygen atoms from adjacent hydroxyl groups by reaction with a reagent.

16. The method according to claim 6, wherein the polyvinyl alcohol is a copolymer of vinyl alcohol and an anionic acrylic monomer.

17. The method according to claim 16, wherein the anionic acrylic monomer is acrylic acid.

18. The method according to claim 1, in which the composition which is introduced into the brain comprises a radiosensitizing agent.

19. The method according to claim 18, wherein the chemotherapeutic agent is the radiosensitizing agent.

20. The method according to claim 1, wherein in the treatment the composition is injected into the resection margin of a debulked tumor in the brain.

21. The method according to claim 1, wherein in the treatment the composition is injected directly into the brain tumor.

22. The method according to claim 15, wherein the pendent ethylenic groups are derived from N-acrylamino acetaldehyde dimethyl acetal.

23. The method according to claim 1, wherein the polymer has an equilibrium water content of 40 to 99 wt %.

24. The method according to claim 23, wherein the polymer has an equilibrium water content of 75 to 95 wt %.

25. The method according to claim 1, wherein the microspheres have sizes of 100-300 μm.

* * * * *